United States Patent [19]
Woodson

[11] Patent Number: 5,739,004
[45] Date of Patent: Apr. 14, 1998

[54] BIOLOGICAL STERILIZATION INDICATION FOR USE WITH OR WITHOUT TEST PACK MATERIALS OR DEVICES

[75] Inventor: Lewis P. Woodson, Apple Valley, Minn.

[73] Assignee: Minnesota Mining and Manufacturing Company, St. Paul, Minn.

[21] Appl. No.: 739,277

[22] Filed: Oct. 29, 1996

Related U.S. Application Data

[63] Continuation of Ser. No. 450,853, May 25, 1995, abandoned, which is a continuation-in-part of Ser. No. 233,714, May 5, 1994, abandoned, which is a continuation-in-part of Ser. No. 64,946, May 20, 1993, abandoned.

[51] Int. Cl.$^6$ .............................. C12Q 1/22; C12M 1/40
[52] U.S. Cl. .................... 435/31; 435/4; 435/14; 435/24; 435/29; 435/288.1; 435/291.1; 435/810; 435/832; 435/839; 422/58; 422/60; 422/61; 422/102
[58] Field of Search ........................ 435/31, 4, 14, 435/24, 29, 288.1, 291.1, 810, 832.1, 839; 422/581, 60, 61, 102

[56] References Cited

U.S. PATENT DOCUMENTS

| | | | |
|---|---|---|---|
| 2,854,384 | 9/1958 | Beakley et al. | 435/296 |
| 3,239,429 | 3/1966 | Menolasino et al. | 435/296 |
| 3,346,464 | 10/1967 | Ernst | 435/31 |
| 3,440,144 | 4/1969 | Andersen | 435/296 |
| 3,585,112 | 6/1971 | Ernst | 435/31 |
| 3,661,717 | 5/1972 | Nelson | 435/296 |
| 3,752,743 | 8/1973 | Henshilwood | 435/31 |
| 3,846,242 | 11/1974 | Ernst | 435/31 |
| 4,147,767 | 4/1979 | Yapel, Jr. | 424/22 |
| 4,291,122 | 9/1981 | Orelski | 435/31 |
| 4,304,869 | 12/1981 | Dyke | 435/296 |
| 4,311,793 | 1/1982 | Halleck | 435/31 |
| 4,416,984 | 11/1983 | Wheeler, Jr. | 435/31 |
| 4,461,837 | 7/1984 | Karle et al. | 435/296 |
| 4,528,268 | 7/1985 | Andersen et al. | 435/31 |
| 4,579,823 | 4/1986 | Ryder | 435/291 |
| 4,580,682 | 4/1986 | Gorski et al. | 206/569 |
| 4,596,773 | 6/1986 | Wheeler, Jr. | 435/31 |
| 4,636,472 | 1/1987 | Bruso | 435/287 |
| 4,663,287 | 5/1987 | Barker . | |
| 4,717,661 | 1/1988 | McCormick et al. | 435/31 |
| 4,739,881 | 4/1988 | Bruso | 206/305 |
| 4,743,537 | 5/1988 | McCormick et al. | 435/296 |
| 4,828,797 | 5/1989 | Zwarun et al. | 422/55 |
| 4,839,291 | 6/1989 | Welsh et al. | 435/296 |
| 4,885,253 | 12/1989 | Kralovic | 435/296 |
| 4,918,003 | 4/1990 | Macaro et al. | 435/31 |
| 5,073,488 | 12/1991 | Matner et al. | 435/31 |
| 5,223,401 | 6/1993 | Foltz et al. | 435/18 |
| 5,252,484 | 10/1993 | Matner et al. | 435/288 |
| 5,418,167 | 5/1995 | Matner et al. | 435/288 |

FOREIGN PATENT DOCUMENTS

| | | |
|---|---|---|
| 0 152 298 A3 | 8/1985 | European Pat. Off. . |
| 0 255 229 A2 | 2/1988 | European Pat. Off. . |
| 0 414 968 A1 | 3/1991 | European Pat. Off. . |
| 0 419 282 A1 | 3/1991 | European Pat. Off. . |
| 0 421 760 A1 | 4/1991 | European Pat. Off. . |
| 0 433 053 A1 | 6/1991 | European Pat. Off. . |
| 2 113 389 | 8/1983 | United Kingdom . |

OTHER PUBLICATIONS

Braun et al., "Use of Dry Sugar in Sweetening Foods Canned in Sirup," *Food Industries*, vol. 13, pp. 64–65 (1941).

Neidleman, S., "Enzymes under Stress," *ASM News*, vol. 55, No. 2, pp. 67–70 (1989).

Amaha et al., "Effects of Carbohydrates, Proteins, and Bacterial Cells in the Heating Media on the Heat Resistance of Clostridium Sporogenes," *Journal of Bacteriology*, vol. 68, No. 3, pp. 338–345 (1954).

Anderson, et al., "Effect of Acids, Salt, Sugar, and Other Food Ingredients on Thermal Resistance of *Bacillus Thermoacidurans*[1]," *Food Res.*, vol. 14, pp. 499–510 (1949).

Smith, et al., "Effect of Environmental Conditions during Heating on Commerical Spore Strip Performance," *Applied and Environmental Microbiology*, vol. 44, No. 1, pp. 12–18 (Jul. 1982).

Sugiyama, H., "Studies on Factors Affecting the Heat Resistance of Spores of Clostridium Botulinum," *Journal of Bacteriology*, vol. 62, pp. 81–96 (1951).

Corry, J., "The Effect of Sugars and Polyols on the Heat Resistance of Salmonellae," *J. Appl. Bact.*, vol. 37, pp. 31–43 (1974).

Luchter–Wasylewska, et al., "Stabilization of Human Prostatic Acid Phosphatase by Coupling with Chondroitin Sulfate," *Biotechnology and Applied Biochemistry*, vol. 13, No. 1, pp. 36–47 (Feb. 1991).

Srivastava, R., "Studies on stabilization of amylase by covalent coupling to soluble polysaccharides," *Enzyme Microb. Technol.*, vol. 13, No. 2, pp. 164–170 (Feb. 1991).

Redway, et al., "Effect of Carbohydrates and Related Compounds on the Long–Term Preservation of Freeze–Dried Bacteria," *Cryobiology*, vol. 11, pp. 73–79 (1974).

Srivastava, R., "Effect of glycosylation of bacterial amylase on stability and active site conformation," *Indian Journal of Biochemistry & Biophysics*, vol. 28, No. 2, pp. 109–113 (Apr. 1991).

"Immobilization Techniques for Enzymes," *Methods in Enzymology—Immobilized Enzymes and Cells*, vol. 135, pp. 58–59 (1987) (ed. Klaus Mosbach).

(List continued on next page.)

*Primary Examiner*—Cecilia J. Tsang
*Assistant Examiner*—Abdel A. Mohamed
*Attorney, Agent, or Firm*—Robert W. Sprague

[57] ABSTRACT

A biological indicator which utilizes immobilization to increase the thermostability of the biomaterial (e.g., microorganism or enzyme) contained within the indicator. Due to the increased thermostability of the biomaterial, the indicator can be utilized to monitor sterilization with or without conventional test pack materials or devices.

60 Claims, 3 Drawing Sheets

OTHER PUBLICATIONS

Annear, D.I., "The Preservation of Bacteria by Drying in Peptone Plugs," *J. Hygiene* (Cambridge), vol. 54, pp. 487–508 (1956).

*AAMI Standards and Recommended Practices*, vol. 2: Sterilization (Copyright 1988) (Association for the Advancement of Medical Instrumentation).

Vesley, D., et al., "Fluorimetric Detection of a *Bscillus stearothermophilus* Spore–Bound Enzyme, α–D–Glucosidase, for Rapid Indication of Flash Sterilization Failure," *Applied and Environmental Microbiology*, vol. 58, pp. 717–719 (Feb. 1992).

Torchilin, et al., "Stabilization of Subunit Enzymes by Intramolecular Crosslinking with Bifunctional Reagents," *Annals New York Academy of Sciences*, vol. 434, pp. 27–30 (1984).

Gottschalk, et al., "Chemically Crosslinked Lactate Dehydrogenase: Stability and Reconstitution after Glutaraldehyde Fixation," *Biotechnology and Applied Biochemistry*, vol 9, No. 5, pp. 389–400 (Oct. 1987).

Lenders, et al. "Chemical Stabilization of Glucoamylase from *Aspergillus niger* against Thermal Inactivation," *Biotechnology and Bioengineering*, vol. 31, pp. 267–277 (1988).

Olsen, et al. "Improvement of bacterial β–glucanase thermostability by glycosylation," *Journal of General Microbiology*, vol. 137, pp. 579–585 (1991).

Ichiba, et al., "Cation–induced thermostability of yeast and *Escherichia coli* pyrophosphatases," *Biochem. Cell Biol.*, vol. 66, pp. 25–31 (Jan. 1988).

Kokufuta, et al., Use of Polyelectrolyte Complex–Stabilized Calcium Alginate Gel for Entrapment of β–Amylase, *Biotechnology and Bioengineering*, vol. 32, pp. 756–759 (1988).

Hoshino, et al., "A study on the thermostability of microencapsulated glucose oxidase," *J. Microencapsulation*, Vo. 6, No. 2, pp. 205–211 (1989).

Wawrzyniak, et al., Glucoamylase Covalently Bound to Acrylic Carriers, *Starch Staerke*, vol. 43, No. 7, pp. 283–288 (1991).

Margolin, et al., "Enzymes in polyelectrolyte complexes—The effect of phase transition on thermal stability," *Eur. J. Biochem.*, vol. 146, No. 3, pp. 625–632 (Feb. 1985).

Leonowicz, et al., "Improvement in stability of an immobilized fungal laccase," *Applied Microbiology and Biotechnology*, vol. 29, No. 2–3, pp. 129–135 (1988).

Germain, et al., "Characterization of a Chemically Modified β–Amylase Immobilized on Porous Silica," *J. Chem Tech. Biotechnol.*, vol. 41, pp. 297–315 (1988).

Guisan, et al., "Immobilization–Stabilization of α–Chymotrypsin by Covalent Attachment to Aldehyde–Agarose Gels," *Biotechnology and Bioengineering*, vol. 38, pp. 1144–1152 (1991).

Barbaric, et al., "Stabilization of Glycoenzymes by Cross–linking of Their Carbohydrate Chains," *Annals New York Academy of Sciences*, vol. 542, pp. 173–179 (1988).

Yapel (Jr.), A.F., "Albumin Microspheres: Heat and Chemical Stabilization," *Methods in Enzymology—Drug and Enzyme Targeting Part A*, vol. 112, pp. 3–18 (1985). (ed. Widder, et al.).

Wasylewksa, et al., "Stabilization of Human Prostate Acid Phosphateise by Crosslinking with Diimidoesters," *ACTA Biochimica Polonica*, vol. 34, No. 2, pp. 145–156 (1987).

Tamura, et al., "Stabilization of the Superoxide–Generating Respiratory Burst Oxidase of Human Neutrophil Plasma Membrane by Crosslinking with 1–Ethyl–3–(3–dimethylaminopropyl) Carbodimide," *Archives of Biochemistry and Biophysics*, vol. 275, No. 1, pp. 23–32 (Nov. 1989).

Baker, et al., "Thermal Stabilization of Fungal β–Glucosidase through Glutaraldehyde Crosslinking," *Biotechnology Letters*, vol. 10, No. 5, 325–330 (1988).

Kozulic, et al., "Preparation of the Stabilized Glycoenzymes by Cross–linking Their Carbohydrate Chains," *Applied Biochemistry and Biotechnology*, vol. 15, No. 3, pp. 265–278 (Oct. 1987).

Gottschalk, et al., "Cheimically Crosslinked Lactate Dehydrogenase: Stability and Reconstitution after Glutaraldehyde Fixation," *Biotechnology and Applied Biochemistry*, vol. 9, No. 5, pp. 389–400 (Oct. 1987).

Grunwald, J., et al., "Immobiliztion of Alcohol Dehydrogenase, Malic dehydrogenase and destran–NAD$^+$ Within Nylon–Polyethyleneimine Microcapsules: Preparation and Cofactor Recycling," *Journal of Molecular Catalysis*, vol. 11, p. 83–90 (1981).

Wadiak, D.T., et al., "Kinetic Behavior of Microencapsulated β–Galactosidase," *Biotechnology and Bioengineering*, vol. 17, pp. 1157–1181 (1975).

Yu, Y., et al., "Immobilization of multienzymes and cofactors within lipid–polyamide membrance microcapsules for the multistep conversion of lipophilic and lipophobic substrates," *Enzyme and Microbiological Technology*, vol. 4, pp. 327–331 (Sep. 1982).

Ortmanis, et al., "Study of microencapsulated urease in a continuous feed, stirred tank reactor," *Enzyme and Microbiological Technology*, vol. 6, pp. 135–139 (Mar. 1984).

O'Grady, P., et al., "Microencapsulation of bovine liver arginase: characterization and in viro evaluation of its effect on the growth of the L1210 murine leukaemia," *Enzyme and Microbiological Technology*, vol. 3, pp. 149–152 (Apr. 1981).

Suzuki, Y., et al., "Assignment of a p–Nitrophenyl–α–D–Glucopyranoside–Hydrolyzing α–Glucosidase of *Bacillus Cereus* ATCC 7064 to an Exo–Oligo–1.6 Glucosidase," *Biochimica et Biophysica Acta*, vol. 704, pp. 476–483 (1982).

Technical Bulletin, 3M, Infection Control Products, "1278 Attest™ EO Pack Technical Report," Jan., 1990.

Technical Bulletin, 3M Infection Control Products, "1276 Attest™ Steam Pack Technical Report," Feb., 1988.

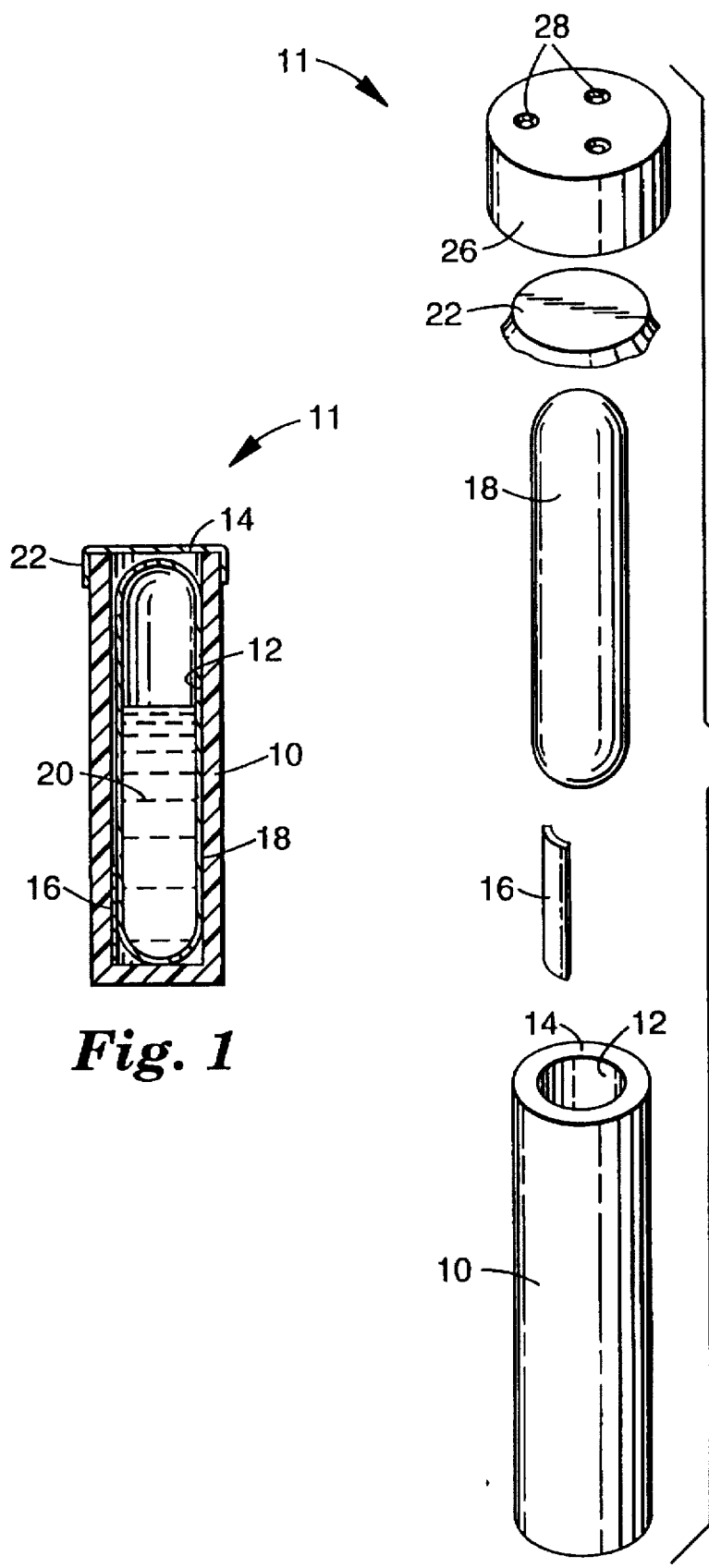

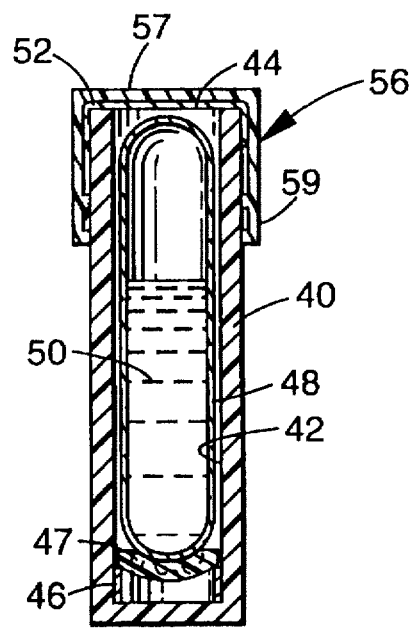
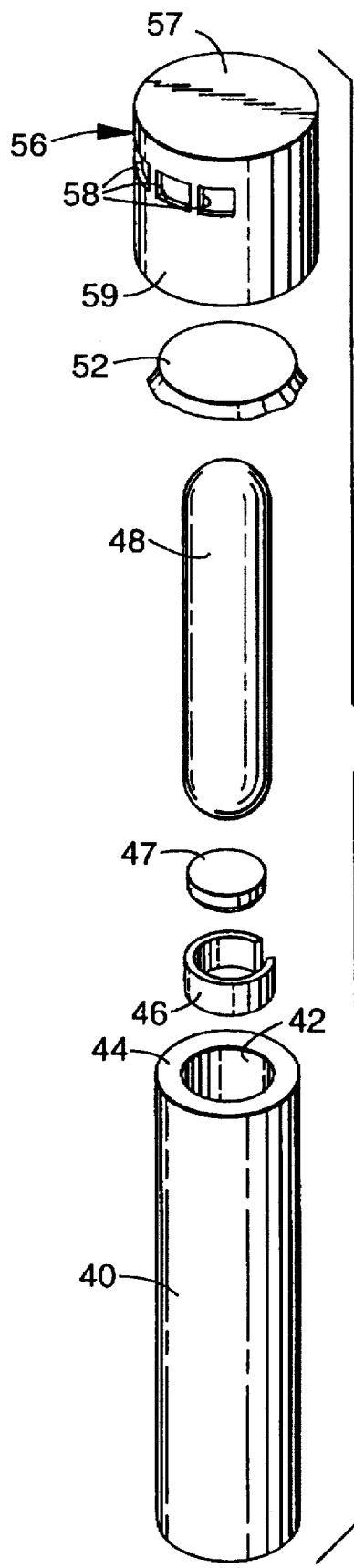
*Fig. 3*
*Fig. 4*

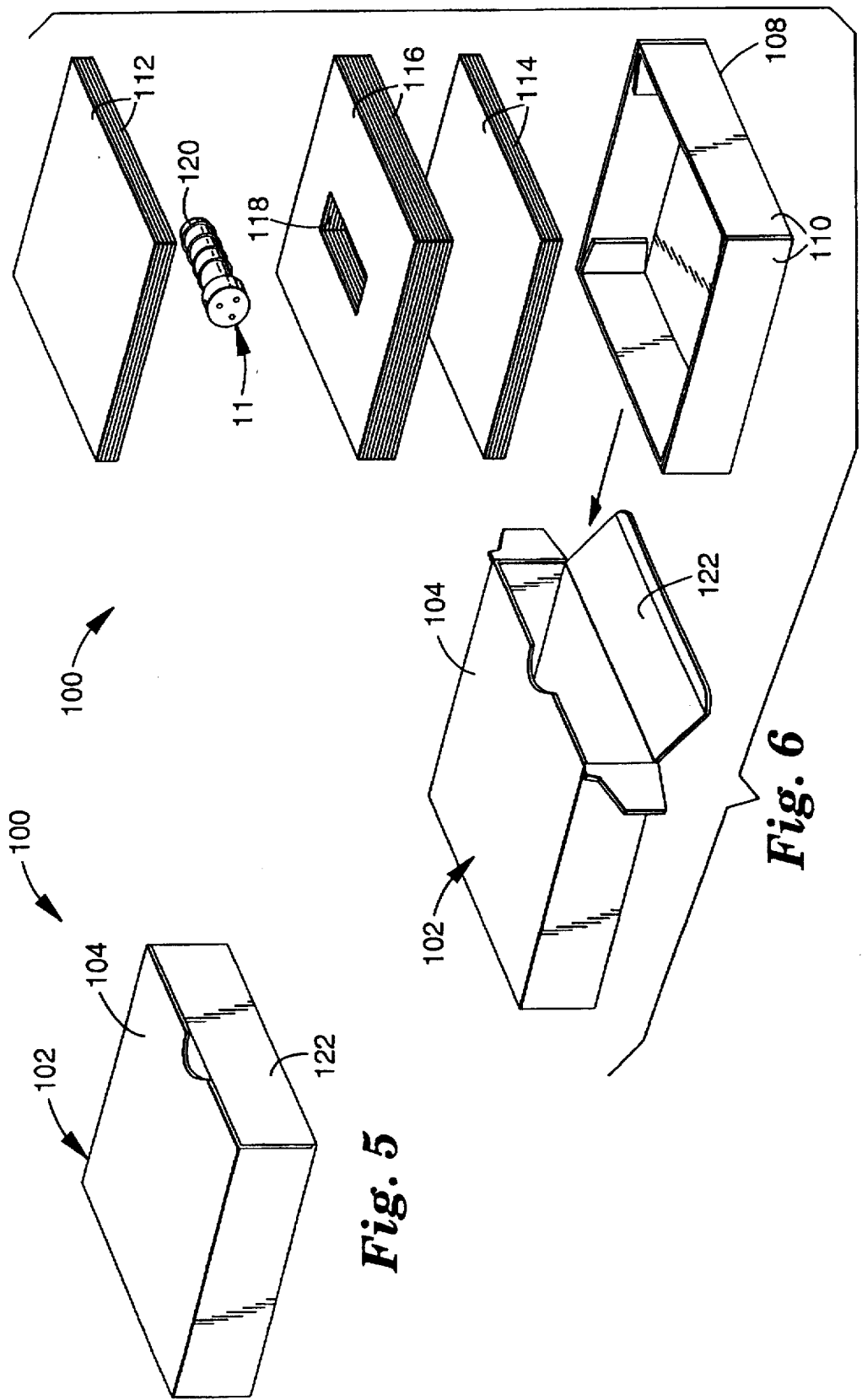

5,739,004

BIOLOGICAL STERILIZATION INDICATION FOR USE WITH OR WITHOUT TEST PACK MATERIALS OR DEVICES

CROSS-REFERENCE TO RELATED APPLICATION

This application is a continuation of application Ser. No. 08/450,863, filed May 25, 1994, abandoned which is a continuation-in-part of U.S. application Ser. No. 08/233,714, filed May 5,1994, abandoned which is a continuation-in-part of U.S. application Ser. No. 08/064,946, filed May 20, 1993, abandoned.

FIELD OF INVENTION

The present invention relates to a biological indicator which utilizes immobilization to increase the thermostability of the biomaterial (e.g., microorganism or enzyme) contained within the indicator. The biological indicator can be utilized to give a read-out of sterilization efficacy either with or without test pack materials or devices.

BACKGROUND OF THE INVENTION

Biological indicators used to determine the efficacy of sterilization are well known in the art. In conventional biological indicators, a test organism which is more resistant to the sterilization process employed than most organisms which would be present by natural contamination is coated on a carrier and subjected to a sterilization cycle along with the articles to be sterilized. After completion of the sterilization cycle, the carrier is incubated in nutrient medium to determine whether any of the test organisms survived the sterilization procedure.

Several procedures have been proposed to test the efficacy of sterilization equipment using biological indicators. The Association for the Advancement of Medical Instrumentation (AAMI) has published recommendations (incorporated herein by reference) for evaluating both ethylene oxide and steam sterilizers. For qualification testing of an ethylene oxide sterilizer, AAMI recommends placing a biological indicator into the barrel of a plastic syringe. A plastic airway, a length of latex tubing, and two of said syringes are placed in the center of a stack of folded surgical towels. The stack is then wrapped in a wrapping material. The resulting test pack is designed to challenge the parameters of ethylene oxide sterilization.

The AAMI's recommendations for a test pack for use in steam gravity displacement and prevacuum sterilizers include using an appropriate biological indicator in a 14 to 16 towel test pack. The towels are folded and stacked. The biological indicator should be placed between the seventh and eighth towels in the geometric center of the pack.

Test packs containing biological indicators and other materials are intended to challenge all of the parameters necessary for evaluation of efficacy of ethylene oxide and steam sterilizers. One requirement of both types of AAMI test packs is to impede the flow of sterilant to the biological indicator to more closely simulate the rate of sterilization experienced by the load. Although effective for its intended purpose, the construction of an AAMI test pack for ethylene oxide and steam sterilization cycles is labor intensive and the resulting pack is bulky. In light of these limitations, several commercially available products address the need for a single pre-assembled and standardized composite sterilization test pack. Exemplary products include the "1278 Attest™ EO Pack" and "1276 Attest™ Steam Pack", both commercially available from 3M, and those devices disclosed in U.S. Pat. Nos. 4,739,881; 4,828,797; 4,839,291; 4,636,472; 4,918,003; and in European Patent Nos. 421,760; 419,282; and 255,229.

SUMMARY OF THE INVENTION

The present invention provides, for the first time, a simple biological indicator device which can be used without towels, syringes or other bulky test pack materials and provides sterilization evaluations which are equivalent to or better than those of the prior art devices.

The present invention provides a biological indicator comprising (a) an outer container having liquid impermeable walls, said container having at least one opening therein, (b) contained within said outer container a detectable amount of an immobilized (1) viable test microorganism, or (2) other source of active test enzyme known to be useful to monitor sterilization, which microorganism or enzyme has been immobilized to an extent capable of allowing a detectable amount of said immobilized microorganism or enzyme to survive or remain active following a sterilization cycle which is sublethal to test microorganisms contained in a test pack commonly used to monitor sterilization. Yet, incapable of allowing any detectable amount of immobilized microorganism or enzyme to survive or remain active following a sterilization cycle which is lethal to the test microorganisms contained in the test pack commonly used to monitor sterilization.

The invention further provides a test pack for determining the efficacy of a sterilization cycle in a sterilization chamber comprising the biological indicator of this invention within a test pack commonly used to monitor sterilization.

Additionally, the invention provides a method of increasing the thermostability of a (1) viable microorganism commonly used to monitor sterilization, or (2) another source of an active test enzyme known to be useful to monitor sterilization, within a biological indicator comprising immobilizing the test microorganism and/or active enzyme.

The prior art discloses a number of methods of immobilizing various microorganisms and enzymes (e.g., U.S. Pat. No. 4,663,287; Srivastava, *Indian Journal of Biochemistry and Biophysics*, Vol. 28, pp. 109–113 (April 1991); *Biotechnology and Applied Biochemistry*, Vol. 13, pp. 36–47 (1991); *American Society for Microbiology News*, Vol. 55, pp. 67–70 (1989); *Journal of Hygiene*, Vol. 54(4), pp. 487–508 (1956); *Food Industries*, March 1941, pp. 64–65; *Food Research*, Vol. 14., pp. 499–510 (1949); *Journal of Bacteriology*, Vol. 62, pp. 81–96 (1951); *Journal of Bacteriology*, Vol. 68, pp. 338–345 (1954); *Journal of Applied Bacteriology*, Vol. 37, pp. 31–43 (1974). However, none of these references disclose the use of immobilization to stabilize or protect biomaterial in dried form in a biological indicator from the lethal or inactivating effects of either steam or ethylene oxide sterilization. The devices of the present invention are useful to determine the efficacy of a sterilization cycle in either gravity or prevacuum steam sterilizers or ethylene oxide sterilizers and are sufficiently accurate to pass AAMI standards. In preferred embodiments, the devices of the present invention are disposable, pre-assembled, small, easy to use and convenient to handle.

BRIEF DESCRIPTION OF THE FIGURES

FIG. 1 is a cross-sectional view of one embodiment of a biological indicator of the present invention, with the closure device 26 removed.

FIG. 2 is an exploded perspective view of the biological indicator of FIG. 1, closure device 26 included.

FIG. 3 is a cross-sectional view of a preferred embodiment of an indicator of the present invention, with closure 56 in the closed position.

FIG. 4 is an exploded perspective view of the indicator of FIG. 3.

FIG. 5 is an exploded view of a test pack, including a biological indicator of the invention.

FIG. 6 is a perspective view of the test pack of FIG. 5.

DETAILED DESCRIPTION

Microorganisms which may be employed in the biological indicators of the present invention are those conventionally used microorganisms which are generally many times more resistant to the sterilization process being employed than most organisms encountered in natural contamination. Favorable results have been obtained with bacteria and fungi which exist in both "spore" and "vegetative" states. The bacterial spore is recognized as the most resistant form of microbial life. It is the life form of choice in all tests for determining the sterilizing efficacy of devices, chemicals and processes. Spores from Bacillus and Clostridia species are the most commonly used to monitor sterilization processes utilizing saturated steam, dry heat, gamma irradiation and ethylene oxide.

Particularly preferred microorganisms include *Bacillus stearothermophilus*, *Bacillus subtilis*, and *Bacillus pumilus*. *Bacillus stearothermophilus* is particularly useful to monitor sterilization under steam sterilization conditions. *Bacillus subtilis* is particularly useful to monitor conditions of gas and dry heat sterilization. *Bacillus pumilus* is particularly useful to monitor gamma irradiation sterilization.

In a preferred biological embodiment of the present invention, the biological indicator includes a source of active immobilized enzyme.

The enzymes useful in the preferred embodiment are enzymes including extracellular and intracellular enzymes, whose activity correlates with the viability of at least one microorganism commonly used to monitor sterilization efficacy. The use of such enzymes to monitor sterilization efficacy is described in commonly assigned U.S. Pat. No. 5,073,488, incorporated herein by reference. After the indicator is subjected to a sterilization cycle the immobilized enzyme contained therein is mixed with an aqueous reaction mixture of a substrate for that enzyme. The reaction mixture is then evaluated in, e.g., a fluorometer or a colorimeter, to determine the presence of any enzyme-modified product. The existence of detectable enzyme-modified product above background within an established period of time (dependent upon the identity of the enzyme and the substrate, the concentration of each, and the incubation conditions) indicates a sterilization failure. The lack of detectable enzyme-modified product within the established period of time indicates a sterilization cycle which would have been lethal to the test organism and is therefore adequate.

Enzymes which have been found to be useful include hydrolytic enzymes from spore-forming microorganisms, as well as enzymes derived from animals or plants, such as almonds. Such enzymes include beta-D-glucosidase, alpha-D-glucosidase, alkaline phosphatase, acid phosphatase, butyrate esterase, caprylate esterase lipase, myristate lipase, leucine aminopeptidase, valine aminopeptidase, chymotrypsin, phosphohydrolase, alpha-D-galactosidase, beta-D-galactosidase, alpha-L-arabinofuranosidase, N-acetyl-β-glucosaminidase, beta-D-cellobiosidase, alanine aminopeptidase, proline aminopeptidase, tyrosine aminopeptidase, phenylalanine aminopeptidase, beta-D-glucuronidase, and fatty acid esterase derived from spore-forming microorganisms, such as Candida, Bacillus, Neurospora, and Clostridium species of microorganisms.

The source of active enzyme may be:

1) the purified, isolated enzyme derived from an appropriate microorganism;
2) a microorganism to which the enzyme is indigenous or added by genetic engineering; or
3) a microorganism to which the enzyme has been added during sporulation or growth, such that the enzyme is incorporated or associated with the microorganism, e.g., an enzyme added to a spore during sporulation which becomes incorporated within the spore.

Advantageously, a microorganism which is itself one conventionally used to monitor sterilization conditions, is utilized as the source of active enzyme. Any of the microorganism which remains viable, following the completion of the sterilization cycle, is incubated with nutrient growth medium to confirm by conventional technique whether the sterilization conditions had been sufficient to kill all of the microorganisms in the indicator, indicating that the sterilization conditions had been sufficient to sterilize all of the items in the sterilizer.

A number of different means of immobilizing the microorganism or enzyme (referred to herein as the "biomaterial") may be utilized. One particularly useful technique is to chemically immobilize the microorganism or enzyme using compounds (referred to herein as "immobilizing agents") which 1) form ionic and/or covalent bonds to the microorganism or enzyme thereby forming a stable immobilized complex; 2) coat or entrap the molecules of the biomaterial (referred to herein as the "biomolecules") with a hygroscopic or hydrophilic layer which protects against denaturation; or 3) dehydrate the outer membrane of the biomolecule to increase its thermostability.

Particularly useful immobilizing agents for use in steam sterilization include alditols, di and trisaccharides and polymeric alcohols selected from polyvinyl alcohol, glycols and diols. For ethylene oxide sterilization, suitable immobilizing compounds include alditols; monosaccharides, including aldoses and ketoses; polysaccharides, such as di, tri, tetra, penta and hexasaccharides, starches, cyclodextrins, pectins, guar gum, gum tragantha, gum arabic, celluloses and kappa carrageenan; polylactams, such as polyvinyllactams; and the polymeric alcohols described above.

The alditols and monosaccharides preferably consist of 3 to 6 carbon atoms. The di and trisaccharides preferably have at least 4 carbon atoms per saccharide unit and the other polysaccharides preferably have 5 or 6 carbon atoms per saccharide unit. Preferably the alditols and saccharides have molecular weights of between about 100 and 100,000 daltons. The saccharides may be reducing or nonreducing saccharides. Preserved polymeric alcohols have molecular weights of between about 200 and 100,000 daltons. Preferred polylactams have molecular weights of about 50 to 100,000 daltons.

Particularly preferred alditols include glycerol, threitol, ribitol (commonly known as adonitol), arabinitol, xylitol, allitol, glucitol (commonly known as sorbitol), mannitol, iditol, galactitol (commonly known as dulcitol), altritol, erythitol, inositol, heptitol, octitol, nonitol, decitol, dodecitol, stracitol, and polyalitol.

Particularly preferred aldoses include glyceraldehyde, threose, erythrose, ribose, arabinose, xylose, lyxose, allose, altrose, glucose, mannose, gulose, idose, galactose, talose, heptose, octose, nonitose, decitose, dodecitose, rhamnose, fucose, 2-deoxyribose, glucosamine, galactosamine, 3-dimethylamino-3, 6-dideoxyaltose, and 3-amino-3-deoxyribose.

Particularly preferred ketoses include dihydroxyacetone, erythrulose, ribalose, xylolose, psicose, fructose, sorbose and tagatose.

Particularly preferred disaccharides include arabinopyranobiose, arabinofuranobiose, cellobiose, cellubiouronic acid, chitobiose, chondrosine, galactobiose, galacturonic acid, gentobiose, glucosylgalactose, glucosylglucosamine, hyalobiouronic acid, inulobiose, isomaltose, kojibiose, lactose, laminarabiose, maltose, mannobiose, melibiose, 4-methylglucosylxylose, nigerose, planteobiose, primaverose, rutinose, sophorose, sucrose, trehalose, tufanose, vicianose, and xylobiose.

Particularly preferred trisaccharides include cellotriose, gentaianose, 6-O-glucosylmaltose, isokestose, isomaltotriose, isopanose, kestose, laminaratriose, maltotriose, melezitose, neokestose, neuraminolactose, panose, planteose, raffinose, and umbelliferose.

Particularly preferred tetrasaccharides include cellotetraose, maltotetraose, and stachyose. A particularly preferred pentasaccaride is verbascose. Other preferred polysaccharides include cyclic oligosaccharides, such as cyclomatohexaose, cyclomaltoheptaose and cyclomaltooctaose; celluloses, such as methylcelluose, hydroxypropyl methyl cellulose, carboxymethylcellulose, and hydroxypropyl cellulose; gums; mucilages; pectins; hemicelluloses; lipopolysaccarides; glycogen; chitin; and starch.

Particularly preferred polymeric alcohols include polyvinyl alcohol, propylene glycol, dipropylene glycol, polyethylene glycol (m.w. 200–100,000 daltons), polypropylene glycol (m.w. 200–10,000 daltons), ether alcohols, such as polyethylene glycol ether (m.w. 500–50,000 daltons), polypropylene glycol ether (m.w. 500–10,000 daltons), and diols, such as 1,3-butanediol, 1,5-pentanediol, 1,6-hexanediol, 1,7-heptanediol, 1,8-octanediol, 1,9-nonanediol and 1,10-decanediol.

Particularly preferred polyvinyl lactams include N-vinyl-2-pyrrolidone, 5-methyl-N-vinyl-2-pyrrolidone, 5-ethyl-N-vinyl-2-pyrrolidone, 3,3-dimethyl-N-vinyl-2-pyrrolidone, 3-methyl-N-vinyl-2-pyrrolidone, 3-ethyl-N-vinyl-2-pyrrolidone, 4-methyl-N-vinyl-2-pyrrolidone, 4-ethyl-N-vinyl-2-pyrrolidone, N-vinyl-2-valerolactam, and N-vinyl-2-caprolactam.

The immobilizing compounds or agents are preferably utilized as coatings over microorganisms or enzymes contained on conventional carriers. Alternatively, suspensions of the test microorganisms or enzymes in the immobilizing agents are prepared and these suspensions are coated upon conventional carrier strips and allowed to dry. The amount of immobilizing agent applied to the biomaterial is preferably about $1 \times 10^{-6}$ to $1 \times 10^{-12}$ g/spore or unit of enzyme, more preferably about $1 \times 10^{-9}$ to $1 \times 10^{-11}$ g/spore or unit of enzyme, and most preferably $9 \times 10^{-10}$ to $1 \times 10^{-10}$ g/spore or unit of enzyme. Preferably aqueous solutions of the immobilizing agent in concentrations of 0.1 to 98 percent w/v, more preferably 1 to 70 percent w/v and most preferably 5 to 50 percent w/v are applied to the biomaterial. Preferably also the immobilizing agent is applied to the biomaterial so that the substrate upon which the dried biomaterial is carried includes immobilizing agent at coating weight, of preferably about $1 \times 10^{-1}$ to $1 \times 10^{-7}$ g/mm$^2$, more preferably about $1 \times 10^{-4}$ to $1 \times 10^{-6}$ g/mm$^2$, and most preferably $9 \times 10^{-5}$ to $1 \times 10^{-5}$ g/mm$^2$.

The following tables list particularly preferred concentrations of a number of immobilizing agents in aqueous solution to be utilized to prepare stand alone biological indicators (BI) (i.e., without the use of towels, syringes or other test pack materials or devices) and biological indicators to be used in conventional test packs, for use in steam and ethylene oxide sterilization cycles.

For monitoring steam sterilization using 121° C. gravity or 132° C. prevacuum cycles:

| Immobilizing Agent | Concentration for Stand Alone VI (w/v) | Concentration for Test Pack (w/v) |
|---|---|---|
| Monosaccharides | | |
| sorbitol | 20–98% | 0.1–19% |
| adonitol | 30–70% | 0.1–29% |
| xylitol | 20–70% | 0.1–19% |
| erythitol | 30–70% | 0.1–29% |
| glycerin | 10–98% | 0.1–9% |
| d-mannitol | 15–70% | 0.1–14% |
| myo-inositol | 10–70% | 0.1–9% |
| dulcitol | 5–70% | 0.1–4% |
| arabinitol | 10–70% | 0.1–9% |
| Disaccharides | | |
| lactose | 50–98% | 0.1–49% |
| cellobiose | 20–70% | 0.1–19% |
| maltose | 40–98% | 0.1–39% |
| Trisaccharides | | |
| raffinose | 40–98% | 0.1–39% |
| melezitose | 30–70% | 0.1–29% |
| Polymeric Alcohols | | |
| polyethylene glycol | 15–70% | 0.1–14% |
| polyvinyl alcohol | 0.75–5% | 0.1–0.74% |

In more stringent steam sterilization cycles (e.g. 121° C. or 134° C. prevacuum) the concentration of immobilizing agent for biological indicators in test packs may need to be increased by four to five times that indicated above.

For monitoring ethylene oxide sterilization:

| Immobilizing Agent | Concentration for Stand Alone BI (w/v) | Concentration for Test Pack (w/v) |
|---|---|---|
| Monosaccharides | | |
| glucose | 20–98% | 0.1–19% |
| ribose | 30–90% | 0.1–29% |
| arabinose | 5–70% | 0.1–4% |
| erythitol | 5–70% | 0.1–4% |
| glycerin | 10–98% | 0.1–9% |
| sorbitol | 10–98% | 0.1–9% |
| adonitol | 20–70% | 0.1–19% |
| xylitol | 5–70% | 0.1–4% |
| d-mannitol | 10–70% | 0.1–9% |
| myo-inositol | 10–70% | 0.1–9% |
| dulcitol | 5–70% | 0.1–4% |
| arabinitol | 10–70% | 0.1–9% |
| sorbose | 5–98% | 0.1–4% |
| fructose | 10–98% | 0.1–9% |
| Disaccharides | | |
| cellobiose | 10–70% | 0.1–9% |
| lactose | 10–98% | 0.1–9% |
| sucrose | 10–98% | 0.1–9% |
| trehalose | 20–98% | 0.1–19% |
| maltose | 20–98% | 0.1–29% |
| Trisaccharides | | |
| raffinose | 20–98% | 0.1–19% |

-continued

| Immobilizing Agent | Concentration for Stand Alone BI (w/v) | Concentration for Test Pack (w/v) |
|---|---|---|
| melezitose | 10–70% | 0.1–9% |
| Polysaccharides | | |
| pectin | 0.75–5% | 0.1–0.7% |
| gum guar | 0.5–5% | 0.1–0.4% |
| gum arabic | 0.75–5% | 0.1–0.7% |
| gum tragacantha | 0.75–5% | 0.1–0.7% |
| kappa carragenan | 0.75–5% | 0.1–0.7% |
| starch | 10–70% | 0.1–9% |
| Polymeric Alcohols | | |
| dipropylene glycol | 20–98% | 0.1–19% |
| polyvinylpyrolidone | 0.75–5% | 0.1–0.7% |
| polyvinyl alcohol | 0.75–5% | 0.1–0.7% |
| polyethylene glycol | 10–70% | 0.1–9% |

Adsorption of the microorganism or enzyme onto a water-insoluble support material is another method of immobilizing the biomolecule. Useful support materials bond to the microorganism or enzyme by weak bonding forces such as salt-linkages, hydrogen bonds and Van der Waals forces, and are capable of adsorbing at least $1 \times 10^2$ microorganisms or 0.1 unit of enzyme. Exemplary support materials include alumina, bentonite, calcium carbonate, calcium phosphate gel, cellulose (such as aminoethyl, carboxymethyl, diethylamino-ethyl, palmitoyl, phenoxyacetyl, phosphate, tonnin-aminohexyl, tonnin-triethylaminoethyl, and triethylaminoethyl celluloses), clay, collagen, dextrans (such as dextran sulfate), dextran derivatives (such as "Sephadex® G-Types", commercially available from Pharmacia), porous glass, hydroxyapatite, koalin, phenolic polymers, silica gel, agarose, "Sepharose® Ion Exchangers", commercially available from Pharmacia (such as concanavalin A-Sepharose) "Sephadex® Ion Exchanger", commercially available from Pharmacia, carbon (such as activated, glossy, molecular sieve 4A, nylon or zeolite carbon), stainless steel, silochrome, titanium oxide, polystyrene and polypropylene.

Enzymes or microorganisms can also be immobilized by water-insoluble support materials which form bonds to the biomolecule. Such support materials include groups which react with functional groups on the molecules of biomaterial (or biomolecules), such as the alpha- or epsilon-groups of lysine, tyrosine, histidine, arginine or cysteine, so as to bond to at least $1 \times 10^2$ microorganisms or 0.1 unit of enzyme. Useful support materials which form covalent bonds to biomolecules have covalent bonding groups such as hydroxyl, amino, carboxyl or sulfonic acid groups. Particularly useful support materials for this type of immobilization include agarose, cellulose, dextran, glass, polyacrylamide co-polymers, polyamino styrene, collagen, polyhydroxyalkylmethacrylate, silica, polyethylene, polyester, polystyrene, nylon, alkyl anhydride polymers, polythiol/4-vinylpyridine, gelatin, polyvinyl alcohol, polyethylene terephthalate, polyacrylonitrile, chitin, polyurethane, carbon, silochrome, titania, ferrite, alumina, magnetic iron particles.

Useful support materials which form ionic bonds to biomolecules also have functional groups such as hydroxyl, amino, carboxyl or sulfonic acid groups. Particularly useful support materials for this type of immobilization are described in references such as "Immobilized Enzymes and Cells", K. Mosbach, Academic Press, Inc. (1987), and include ionic celluloses, such as aminoethyl, carboxymethyl, diethylaminoethyl and triethylaminoethyl celluloses, ionic polystyrene (such as those available as "Amberlite" from Mallinckrodt Chemical Works, St. Louis, Mo.), dextran sulfate, and "Sephadex® Ion Exchangers", such as carboxymethyl, diethylaminoethyl, quaternaryaminoethyl and sulfopropyl "Sephadex® Ion Exchangers", commercially available from Pharmacia.

To immobilize using the support materials, the microorganism or enzyme is mixed with the support material in an aqueous medium at a pH which does not inhibit enzyme activity. Following a period of incubation, the insoluble support material with adsorbed or attached biomaterial is separated from the mixture by centrifugation or filtration. The solid recovered is then used as a carrier for immobilized biomaterial in biological indicator devices.

Another method of immobilizing enzymes or microorganisms is to entrap the biomaterial in a chemically crosslinked polymer gel matrix. The gel is usually comprised of non-ionic polymer-forming materials which are non-reactive with enzymes or microorganisms and are capable of entrapping at least $1 \times 10^2$ microorganisms or 0.1 unit of enzyme. Exemplary gels include polyacrylamide gels, polyacrylamide-hydrazide gels, calcium alginate gels, kappa-carrageenan gels, agar gels, collagen, cellulose gels, chitosan gels, and methacrylate gels.

A still further means of immobilizing microorganisms and enzymes is micro-encapsulation, whereby an artificial membrane is created around the biomolecule. Since the membrane forming process does not depend upon the particular biomolecule in solution, a number of membrane-forming materials may be used to encapsulate a variety of enzymes and microorganisms. Exemplary materials capable of microencapsulating biomolecules include cellulose acetate butyrate, cellulose nitrate, lipid-polyamide, polyethyleneimine-nylon, nylon, bovine serum albumin, polyvinylpyrolidone, poly(phthaloylpiperazine) and epoxy. Typical methods of encapsulation are described in *Journal of Molecular Catalysis*, Vol. 11, p. 83 (1981); *Biotechnology and Bioengineering*, Vol. 17, p. 1157 (1975); *Enzyme and Microbiological Technology*, Vol. 4, p. 327 (1982); *Enzyme and Microbiological Technology*, Vol. 6, p. 135 (1984); *Enzyme and Microbiological Technology*, Vol. 3, p. 149 (1981); *Methods in Enzymology*, Vol. 112, pp. 3–112 (1985); and U.S. Pat. No. 4,147,767.

Crosslinking of enzymes or microorganisms through their side amino acid groups is another immobilization method. Immobilizing agents such as dialdehydes, diimido esters, diisocyanates, and bisdiazonium salts are used to form intra- or intermolecular crosslinking of the biomolecules. These agents must be capable of crosslinking at least $1 \times 10^2$ microorganisms or 0.1 unit of enzyme. Useful crosslinking methods are described in *Annals New York Academy of Sciences*, Vol. 542, pp. 173–179 (1988); *Annals New York Academy of Sciences*, Vol. 434, pp. 27–30 (1984); *Biotechnology and Applied Biochemistry*, Vol. 9(5), pp. 389–400 (1987); *Applied Biochemistry and Biotechnology*, Vol. 15(3), pp. 265–278 (1987); *Biotechnology Letters*, Vol. 10(5), pp. 325–330 (1988); *Archives of Biochemistry and Biophysics*, Vol. 275(1), pp. 23–32 (Nov. 15, 1989); and *ACTA Biochimica Polonica*, Vol. 34(2), pp. 145–156 (1987). Crosslinking stabilizes the conformational rigidity of the enzyme or biomolecule, thus preventing the biomolecule from being denatured by such things as heat and moisture.

In summary, any of the immobilization methods described above, i.e., chemical immobilization, adsorption or bonding onto supports, entrapment, encapsulation or crosslinking, or any combination of these methods can be utilized in the practice of this invention. Regardless of the method of immobilization employed, the extent of immobilization required in order for the biological indicator of the present invention to provide results equivalent to AAMI test packs depends upon a number of factors. Such factors include the sterilization cycle parameters (e.g., temperature and sterilant concentration), whether conventional microorganism growth or use of enzyme substrates is used to evaluate sterility, and whether the biological indicator of the invention is used with or without a test pack.

To monitor sterilization with a stand alone biological indicator of the invention (i.e., without the use of towels, syringes or other test pack materials or devices), the microorganism or enzyme is preferably immobilized to an extent capable of allowing a detectable amount of the immobilized biomaterial to survive or remain active following at least a 15 minute exposure to a steam sterilization cycle of 121° C. gravity, yet not capable of allowing any detectable amount of immobilized biomaterial to survive or remain active following an exposure of up to 45 minutes, more preferably up to 30 minutes, to this sterilization cycle. For use as a stand alone biological indicator in a steam sterilization cycle of 132° C. prevacuum, the microorganism or enzyme is preferably immobilized to an extent capable of allowing a detectable amount of the immobilized biomaterial to survive or remain active following at least a fifteen second, more preferably at least a one minute exposure to the cycle, yet not capable of allowing any detectable amount of microorganism or enzyme to survive or remain active following an exposure of up to 15 minutes, more preferably up to 10 minutes to the cycle. For use as a stand alone biological indicator in a steam sterilization cycle of 121° C. prevacuum, the microorganism or enzyme is preferably immobilized to an extent capable of allowing a detectable amount of the immobilized biomaterial to survive or remain active following at least a five minute exposure to the cycle, yet not capable of allowing any detectable amount of microorganism or enzyme to survive or remain active following an exposure to the cycle of up to 15 minutes. In a steam sterilization cycle of 134° C. prevacuum, the microorganism or enzyme in the stand alone device is preferably immobilized to an extent capable of allowing a detectable amount of the immobilized biomaterial to survive or remain active following at least a two second, more preferably at least a fifteen second exposure to the cycle, yet not capable of allowing any detectable amount of microorganism or enzyme to survive or remain active following an exposure to the cycle of up to 10 minutes, more preferably up to 6 minutes.

For use as a stand alone biological indicator in an ethylene oxide sterilization cycle, the microorganism or enzyme is preferably immobilized to an extent capable of allowing a detectable amount of the immobilized biomaterial to survive or remain active following at least a fifteen minute exposure, yet not capable of allowing any detectable amount of the biomaterial to survive or remain active following an exposure of up to 250 minutes to the ethylene oxide sterilization cycle. More preferably in an ethylene oxide sterilization cycle of 600 mg ethylene oxide per liter, 54° C. and 60% relative humidity, the extent of immobilization is such that a detectable amount of biomaterial survives or remains active following at least a 20 minute exposure and no viable or active biomaterial is detected following a 60 minute, most preferably a 40 minute, exposure to the ethylene oxide cycle. In an ethylene oxide sterilization cycle of 800 mg ethylene oxide per liter, 37° C. and 60% relative humidity, it is more preferred that the extent of immobilization is such that a detectable amount of biomaterial survives or remains active following at least a 20 minute exposure and no viable or active biomaterial is detected following a 120 minute exposure, most preferably a 90 minute exposure, to the cycle.

When the biological indicator of this invention is used not as a stand alone device, but with conventional test pack materials (such as in a commercially available test pack or in an AAMI test pack) the degree of immobilization may be reduced since the test pack materials protect the biomaterial by providing a challenge to the sterilant reaching the immobilized biomaterial.

To monitor sterilization with a biological indicator of the invention placed within towels,, syringes or other test pack materials or devices, the microorganism or enzyme is preferably immobilized to an extent that allows the biomaterial when tested in a stand alone device to exhibit the following survival/kill characteristics. Preferably, the extent of immobilization is sufficient to allow a detectable amount of the immobilized biomaterial to survive or remain active following at least a 5 minute exposure to a steam sterilization cycle of 121° C., yet not capable of allowing any detectable amount of immobilized biomaterial to survive or remain active following an exposure of up to 15 minutes. For use with test pack materials in a steam sterilization cycle of 132° C. prevacuum, the microorganism or enzyme in a stand alone device is preferably immobilized to an extent capable of allowing a detectable amount of the immobilized biomaterial to survive or remain active following at least a 20 second exposure to the cycle, yet not capable of allowing any detectable amount of microorganism or enzyme to survive or remain active following an exposure of up to 6 minutes to the cycle. For use with test pack materials in a steam sterilization cycle of 121° C. or 134° C. prevacuum, the microorganism or enzyme in a stand alone device is preferably immobilized to an extent capable of allowing a detectable amount of the immobilized biomaterial to survive or remain active following at least a 5 second exposure to the cycle, yet not capable of allowing any detectable amount of microorganism or enzyme to survive or remain active following an exposure to the cycle of up to 2 minutes.

For use with test pack material in an ethylene oxide sterilization cycle, the microorganism or enzyme in a stand alone device is preferably immobilized to an extent capable of allowing a detectable amount of the immobilized biomaterial to survive or remain active following at least a 15 minute exposure, yet not capable of allowing any detectable amount of the biomaterial to survive or remain active following an exposure of up to 90 minutes to the ethylene oxide sterilization cycle. More preferably in an ethylene oxide sterilization cycle of 600 mg ethylene oxide per liter, 54° C. and 60% relative humidity, the extent of immobilization is such that a detectable amount of biomaterial survives or remains active following at least a 15 minute exposure and no viable or active biomaterial is detected following a 50 minute exposure to the ethylene oxide cycle. In an ethylene oxide sterilization cycle of 800 mg ethylene oxide per liter, 37° C. and 60% relative humidity, it is more preferred that the extent of immobilization is such that a detectable amount of biomaterial survives or remains active following at least a 15 minute exposure and no viable or active biomaterial is detected following a 90 minute exposure to the cycle.

Preferably the method of detecting microorganism viability in the above-described tests is outgrowth in standard nutrient medium after 24 and 48 hours of incubation. The method of detecting enzyme activity is the use of enzyme substrate as described in U.S. Pat. No. 5,073,488, incorporated herein by reference.

The construction of the biological indicator in which the immobilized microorganism or enzyme is contained is not crucial to this invention. Preferably the biological indicator is a unitary biological indicator, i.e., an indicator containing both the immobilized biomaterial and an enzyme substrate and/or nutrient growth medium. Exemplary structures for such indicators are disclosed in U.S. Pat. Nos. 2,854,384; 3,346,464; 3,239,429; 3,440,144; 3,585,112; 3,661,717; 3,752,743; 3,846,242; 4,291,122; 4,304,869; 4,311,793; 4,416,984; 4,743,537; 4,596,773; 4,461,837; 4,528,268; 4,579,823; 4,580,682; 4,596,773; 4,717,661; and 4,885,253; all of which are incorporated herein by reference. A particularly preferred indicator construction is described in commonly assigned U.S. Ser. No. 7/277,570, also incorporated herein by reference. Any of these biological indicators would be useful in the practice of the present invention if the enzyme or microorganism is immobilized as described herein.

The following description is directed to applicant's preferred embodiments. Many variations of the following devices are possible which will nonetheless fall within the scope of the present invention.

Referring now to FIGS. 1 and 2, a preferred biological indicator is shown having an outer container 10 in the shape of cylindrical tube, having liquid impermeable walls 12, which are preferably gas non-adsorptive, and an open end 14. Outer container 10 contains a carrier 16, such as a strip of filter paper, bearing a predetermined amount of active enzyme and/or a predetermined number of viable microorganisms. Outer container 10 also includes a normally sealed, pressure-openable inner container 18, such as a frangible glass ampoule, containing an aqueous nutrient growth medium and/or a suitable enzyme substrate dissolved or suspended in an aqueous buffered solution 20. The aqueous nutrient medium is capable, with incubation, of promoting growth of viable microorganisms when contacted therewith, and preferably contains a microbial growth indicator which provides a change in the color of the solution if viable microorganisms are present, indicating an inadequate cycle. The enzyme substrate is capable of reacting with active enzyme to yield a luminescent, fluorescent, colored or radioactive material. The inner container 18 is preferably snugly retained within the outer container 10 so that very little of the volume of the outer container remains unoccupied. Inner container 18 is separated from the wall 12 of the outer container 10 by the filter paper carrier 16. The open end 14 of the outer container 10 is provided with a gas-transmissive, semi-porous closure member 22, such as a sheet. The closure member 22 may be sealed to the open end 14 of the outer container 10 by, e.g., heat or adhesive sealing, or by means of a closure device 26, such as a cap, (shown removed in FIG. 1) which has three apertures 28 therethrough. During sterilization with a gaseous sterilization agent, the gaseous sterilant permeates the closure member 22 and passes through the interior of the outer container 10 to contact the immobilized biomaterial upon carrier 16.

As shown in FIG. 2, the apparatus of FIG. 1 may be easily assembled by sequentially inserting into the open end 14 of the outer container 10 the carrier 16 and the inner container 18, and sealing the open end 14 of the outer container 10 with closure member 22 by placing closure member 22 over open end 14 and then placing closure device 26 over closure member 22, in closing engagement with outer container 10.

Outer container 10 is made from material which will withstand the high temperatures encountered in steam sterilizers. Conventional steam sterilizers generally reach temperatures on the order of 121° C.–135° C. Additionally, the walls of container 10 must be substantially impermeable to liquids. Outer container 10 is preferably translucent (including "transparent") so that a change in fluorescence or color may be visually observed without disassembling the indicator device. Preferably, also, the outer container 10 is sufficiently deformable so that the pressure-openable inner container 18 is ruptured when the outer container 10 is deformed, by using external pressure. Outer container 10 can be made by injection molding or extruding suitable materials, including polycarbonate, polypropylene, polyamides, polymethylpentenes and various polyesters.

The closure device 26 can be made from any material that will withstand the sterilization temperatures. As in the case of the outer container 10, suitable materials include polycarbonate, polypropylene, polyamides, polymethylpentenes and various polyesters, with polypropylene being preferred.

The immobilized enzymes and/or the microorganisms which are employed in the present invention normally are carried on a suitable carrier 16. It is contemplated, however, that the immobilized biomaterial may be carried by the inner walls of the outer container 10, or the outer walls of the inner container 18, or that when the immobilized biomaterial is contained in a solid support it is merely include within the outer container 10 and there is no need for a carrier 16. The carrier 16 preferably is water-absorbent, such as filter paper, and should not inhibit microorganism growth or enzyme activity. Sheet-like materials such as cloth, nonwoven polypropylene, rayon or nylon, and microporous polymeric materials are especially preferred. However, metal foil substrates, for example, aluminum or stainless steel may be used, as well as substrates of glass (e.g., glass beads or glass fibers), porcelain, or plastic. Additionally, the enzyme carrier can be constructed of a combination of materials such as paper secured to a plastic or glass backing strip.

To assure reproducibility, it is desired that outer container 10 contain a predetermined amount of immobilized biomaterial. Isolated enzyme is obtained by using general methods of protein purification, such as salt fractionation, chromatography and electrophoresis as described in Colowick, S., and Kaplan, N. O. (Eds), *Methods in Enzymology*, Academic Press, New York, Vols. I–VII, (1957–1964), incorporated herein by reference. Preferably the initial concentration of isolated enzyme to be immobilized is between about 0.001 to 10,000 units, more preferably between about 0.01 and 1,000 units of enzyme, and most preferably between about 0.1 and 100 units. Where an immobilized microorganism is utilized, it is likewise desirable to start with a predetermined approximate number of microorganisms. Where the microorganism is *Bacillus stearothermophilus* or *Bacillus subtilis* the preferred number is about $1\times10^2$ to $1\times10^8$ microorganisms. Where the microorganism is *B. stearothermophilus*, about $1\times10^2$ to $1\times10^7$ microorganisms is particularly preferred. Where *B. subtilis* is employed, about $1\times10^6$ to $1\times10^8$ microorganisms is preferred. The enzyme or microorganism is then immobilized in accordance with the methods described herein. Then preferably a suspension having a known volumetric concentration of immobilized microorganism or enzyme is prepared and a predetermined volume of this suspension is used to moisten carrier 16 (e.g., filter paper). Preferably at least $1\times10^2$ immobilized microorganisms or 0.1 unit of immobilized enzyme is placed upon carrier 16. The dried carrier is then used in outer container 10.

Inner container 18 contains an aqueous solution 20 of nutrient growth media and/or an appropriate enzyme substrate. The types of nutrient media usefully employed in the present invention are widely known to the art. Commonly known microbial growth indicators, which change color in the presence of viable microorganisms, are preferably present in at least one of the containers. The growth indicator material preferably is soluble in, and imparts color (upon microorganism growth) to, the aqueous nutrient medium so that a change in color may be easily observed through the translucent walls of the outer container. In addition, when an enzyme substrate is also present, the growth indicator material is preferably selected so that it will not interfere with the color or luminescence of any enzyme-modified product.

Enzyme substrate when present is preferably contained in inner container 18 in a buffered aqueous solution. The aqueous buffer acts as a reaction medium for the residual active enzyme and the enzyme substrate system after the inner container is ruptured. The ionic conditions of the buffered solution should be such that the enzyme and enzyme substrate are not effected. Preferably, an isotonic buffer, such as phosphate buffered saline solution, tris (hydroxylmethyl) aminomethane-HCl solution, or acetate buffer is chosen.

While the enzyme substrate is normally included in pressure-openable inner container 18, it is contemplated that the enzyme substrate in dry form could be included in outer container 10 along with enzyme carrier 16. In fact, the active enzyme and its substrate could be present in dry form in the same carrier 16. In this construction, inner container 18 would preferably carry the aqueous reaction medium necessary for the active enzyme and its substrate to react.

The inner container 18 which contains the aqueous solution 20 of enzyme substrate and/or which contains the aqueous nutrient medium, is of material which is impermeable to gases and liquids and is capable of being opened upon the application of pressure thereto (i.e., "pressure openable") to permit the enzyme substrate and/or nutrient medium to enter the outer container 10. The inner container 18 is preferably of frangible material, such as glass to permit breakage or crushing of the inner container 18 when the outer container 10 is deformed. In another embodiment, the inner container 18 may be sealed with a plug such that the plug is expelled to release the contents of the inner container 18 upon application of pressure. In still another embodiment, the closure device 26 may include an ampoule crushing device, as shown in U.S. Pat. No. 4,304,869, wherein the closure has tabs depending from the bottom of the closure device which upon depression of the closure device serve to crush the ampoule. Similarly, the device of the present invention may be used in a system having an ampoule crushing pin disposed in the bottom of the outer container 10.

Outer container 10 has at least one opening therein to permit ingress of sterilant (e.g., steam, ethylene oxide). This opening is normally closed or plugged with a gas-transmissive, semi-porous means. Suitable means include closure member 22, made of fibrous materials such as cotton, glass wool, cloth, nonwoven webs made from polypropylene, rayon, polypropylene/rayon, nylon, glass or other fibers, filter papers, microporous hydrophobic and hydrophilic films, open celled polymeric foams, and semi-permeable plastic films such as those described in U.S. Pat. No. 3,346,464.

A preferred embodiment of a sterilization indicator of the present invention is illustrated in FIGS. 3 and 4. The device includes an outer container 40, having liquid impermeable and preferably gels non-adsorptive walls 42 and an open end 44. The outer container 40 includes a pressure-openable inner container 48 which contains an aqueous solution 50 of a suitable enzyme substrate and/or an aqueous nutrient medium. The open end 44 of the outer container 40 is covered by a gas-transmissive, semi-porous closure member 52. With that, the similarity between the device depicted in FIG. 1 ends. In the device of FIGS. 3 and 4, the carrier 46 is located at the bottom closed end of the outer container 40, and a barrier 47 is positioned like a plug between the carrier 46 and the pressure-openable inner container 48. The barrier 47 is preferably made from nonwoven webs of fibers such as cotton, rayon, polypropylene, polypropylene/rayon blends, nylon or glass. Most preferably barrier 47 is constructed from a polypropylene nonwoven web, such as "Thinsulate® 200-B brand Thermal Insulation," commercially available from 3M, St. Paul, Minn.

Barrier 47 serves to isolate the carrier 46 from the inner container 48, thus eliminating cold spots where the inner container 48 may be positioned, over the carrier 46. The existence of cold spots can cause condensation to collect on the carrier 46. The condensate may effect the activity of enzyme contained on the carrier 46. Barrier 47 is preferably made from a hydrophobic material so that growing microorganisms and/or enzyme-modified product concentrates around the carrier and does not diffuse rapidly into the area of the container which is on the other side of the barrier. Maintaining a higher concentration of growing microorganisms and/or enzyme-modified product in the lower portion of the indicator enables the product, whether it be luminescent or colored to be detected after a shorter period of incubation than would be the case if the carrier 46 was reacted with the entire contents of inner container 48.

The closure 56 is comprised of a top 57 and depending sidewalls 59. The closure has a hollow body open at the bottom, with the interior diameter of the closure being about equal to the exterior diameter of outer container 40, so that closure 56 may be frictionally engaged over the open end 44 of outer container 40. Cut within the sidewalls 59 are preferably a plurality of windows 58. When the indicator device is placed in a load to be sterilized, the closure 56 is placed over the opening in the outer container in such a manner that the exterior sidewalls 42 of the outer container do not block windows 58. In such a position, sterilant in the sterilizer may enter outer container 40 by flowing through windows 58. Upon completion of the sterilization cycle, the closure may be fully inserted by depressing it to force the sidewalls 42 of the outer container into engagement with the interior surface of top 57 thereby blocking windows 58. The interior of the outer container 40 is then sealed from the outside environment.

In use, the biological indicator depicted in FIGS. 3 and 4 is placed in a sterilizer chamber together with a number of items to be sterilized by, for example, steam or ethylene oxide gas. When the indicator is in the sterilizer, the closure 56 is in the open position, such that windows 58 are open permitting entry of the sterilant. When the sterilizing agent is introduced into the chamber, the sterilant permeates through the closure member 52 and passes barrier 47 to inactivate the enzyme and kill the test microorganisms present on carrier 46. At the end of the sterilization cycle, the sterilant is replaced with filtered air. The sterility indicator is withdrawn from the sterilizer, the closure 56 is fully inserted to block windows 58, and glass ampoule 48 is broken by, for example, finger pressure, causing the aqueous solution of enzyme substrate and/or nutrient growth media to contact the enzyme carrier 46. The indicator is then placed in a suitable incubating environment.

After the appropriate incubation period, the occurrence of a change in color or luminescence is observed or measured spectrophotometrically through the translucent walls 42 of the outer container 40, and indicates that the sterilization cycle had not inactivated all the active enzyme or killed all the microorganisms present on the carrier 46 hence indicating that the sterilization cycle was perhaps insufficient to completely sterilize the items in the sterilizer. The absence of any change in color or luminescence indicates that the sterilization cycle had been sufficient to inactivate all of the enzyme or kill all of the test microorganisms on the carrier 46, and hence was sufficient to sterilize the items in the sterilizer.

The biological indicator of this invention may be utilized in any type of conventionally used test pack materials or devices. Exemplary test packs include the "1278 Attest™ EO Pack" and "1276 Attest™ Steam Pack", both commercially available from 3M, and those devices disclosed in U.S. Pat. Nos. 4,739,881; 4,828,797; 4,839,291; 4,636,472; 4,918,003; and in European Patent Nos. 421,760; 419,282; and 255,229; all incorporated herein by reference. The biological indicator of this invention may also be used in plastic syringes, towel packs or other test pack devices as recommended by AAMI, the British Department of Health Standards, the German Industrial Norm standards and the Committee of European Normalization. Applicant has found that the use of immobilized biomaterial provides test packs which can more readily replicate these standards in more rigorous sterilization conditions, such as a 121° C. gravity and prevacuum and 132° C. and 134° C. prevacuum steam sterilization cycles. This is particularly true where enzyme activity is used to evaluate sterilization efficacy, as described in U.S. Pat. No. 5,073,488.

FIGS. 5 and 6 show a preferred test pack 100 containing the biological indicator 11 of this invention. The test pack 100 is similar to that disclosed in U.S. Pat. No. 4,918,003 and is comprised of a box 102 which may, for example, have overall dimensions of 134 mm by 140 mm by 28 mm. The box is made of bleached sulfate paper unvarnished.

The box contains an open container 108 also made of bleached sulfate paper which is coated on its exterior surfaces with a steam impermeable thermoplastic coating 110 such as a polypropylene laminate. Container 108 is dimensioned to be only slightly smaller than the box 102.

Two stacks of sheets, 112 and 114, of semi-porous material separated by a stack of sheets 116 also of semi-porous material are contained within container 108. Each of the stacks of semi-porous material is preferably formed of filter paper having an approximate basis weight of 214 pounds (97 kg) (per 3,000 square feet (280 m²)) and an approximate thickness of 1 mm per sheet. Stacks 112 and 114 preferably include 20 to 55 sheets of filter paper.

The semi-porous stack 116 may be composed of approximately 16 sheets of filter paper with a 13 mm by 49 mm area 118 cut from the center of each sheet in order to receive biological indicator 11 of this invention. The height of this central core, when assembled and dry, is approximately 10 mm.

In practice applicant's test pack is opened by opening the box flap 122, the top semi-porous sheets are removed and the biological indicator 11 surrounded by a coiled metal spring 120, preferably made of stainless steel, is placed within the cavity in the center portion of the stack. The coiled spring 120 reduces the compression of the filter paper stacks upon the biological indicator 11 during the sterilization cycle so as not to prematurely crush inner container 18. The top sheets are then replaced and the box closed. The box is then placed in a sterilizer with a normal load and run through a conventional cycle.

Failure of the sterilant to penetrate the porous and semi-porous stacks due to the presence of air pockets in the sterilizer or due to insufficient time, temperature, etc., of the sterilization cycle, will prevent the sterilant from killing the microorganisms or inactivating enzyme within the biological indicator.

Once the sterilization cycle is completed, the test pack 100 is removed from the sterilizer, the box flap 122 is opened and the stacks of sheets are removed to provide quick access to the biological indicator 11. The biological indicator is then incubated with the nutrient growth solution and/or enzyme substrate to reveal any change in color or fluorescence.

The test pack of the present invention replicates the steam permeability qualities of the standard biological test pack described in the AAMI standard and reveals a lack of sterility under substantially the same conditions as the standard AAMI test pack.

The biological indicator and test pack of the present invention have been described primarily with reference to sterilizing media such as ethylene oxide, a variety of steam sterilization cycles (including 121° C. prevacuum and gravity, and 132° C. and 134° C. prevacuum) and the like. The indicator is not, however, limited to these uses, and may as well be used to indicate the efficacy of other sterilizing media, such as dry heat, radiation, propylene oxide, methyl bromide, ozone, chlorine dioxide, formaldehyde, and other gaseous and liquid agents.

The invention will be illustrated by the following non-limiting examples.

EXAMPLES

Example 1

This example illustrates that the biological indicators of this invention comprising immobilized spores and enzyme and without the use of a conventional test pack device can provide sterilization efficacy results comparable with conventional biological indicators (BIs) in an AAMI sixteen towel test pack at conditions of both 121° C. (250° F.) gravity and 132° C. (270° F.) prevacuum sterilization exposures.

Preparation of Spore Strips

*Bacillus stearothermophilus* commercially available as "ATCC 7953" from American Type Culture Collection, Rockville, Md., was grown overnight for approximately 16 hours at 58° C. in tryptic soy broth. This culture was used to inoculate the surfaces of agar contained in plates consisting of 8 g/l nutrient broth, 4 g/l yeast extract, 0.1 g/l manganese chloride, and 20 g/l agar at pH of 7.2. Inoculated plates were incubated at 58° C. for 72 hours. Spores were taken from the plates and suspended in sterile distilled water. The spores were separated from vegetative debris by centrifuging the suspension at 7000 rpm at 4° C. for 20 minutes. The supernatant was poured off and the spores were resuspended in sterile distilled water. This cleaning procedure was repeated several times.

The *Bacillus stearothermophilus* spores were coated and dried on 6.35×9.52 mm (¼×⅜ inch) strips of filter paper, commercially available as "S&S #903 Grade Filter Paper" from Schleicher & Schuell, Inc., Keene, NH, at a population of $7.5 \times 10^5$ spores per strip. This was accomplished by preparing a suspension of the spores in water at a concentration of $7.5 \times 10^7$ spores/ml, and pipetting 10 µl of this suspension onto each filter paper strip and allowing the strip to dry under ambient conditions.

Immobilization of Spores

The following method of immobilizing the spores and spore bound enzyme contained on the spore strips was employed. The spore strips of *Bacillus stearothermophilus* were coated with one of the following aqueous chemical immobilizer solutions: "D-Sorbitol," commercially available from Pfizer, New York, N.Y., or "polyethylene glycol commercially available as "Carbowax® PEG-1450" from Union Carbide Corporation, Danbury, Conn., at percent concentrations (w/v) specified in Tables 1 and 2 to obtain coating weights of approximately $2.75 \times 10^{-5}$ to $3.75 \times 10^{-5}$ g/square millimeter per individual strip. This was accomplished by pipetting 50 μl of one of the immobilizer onto the spore strip and allowing the coated spore strips to dry under ambient conditions for 24 hours.

Assembly of Devices of Invention

Devices were constructed as illustrated in FIGS. 3 and 4, with the immobilized spore strip 46 on the bottom of the outer compartment of the vial 42 and a barrier 47 between the enzyme substrate-containing ampoule 48 and the spore strip. A 1.75 cm (11/16 inch) diameter disc of polypropylene blown microfiber material with a weight of 200 g/sq. meter, commercially available as "Thinsulate® 200-B brand Thermal Insulation" from 3M, St. Paul, Minn., was used as the barrier 47. The ampoule 48 contained 0.67 ml of nutrient medium consisting of 17 g of bacteriological peptone and 0.17 g of L-alanine, as well as 0.1 g of the enzyme substrate, 4-methylumbelliferyl-alpha-D-glucoside, commercially available from Sigma Chemical Co., St. Louis, Mo., and 0.03 g of bromocresol purple pH indicator dye per liter of distilled water. The pH of the enzyme substrate and nutrient medium was adjusted to 7.6 with 1.0N sodium hydroxide. The outer container 42 and the closure 56 were made from polypropylene. The outer container 42 was 5.08 cm (2.0 in) long, with an outer diameter of 89 mm (0.335 in) and an internal diameter of 85 mm (0.303 in). The closure 56 was 1.66 cm (0.510 in) with an internal diameter of 1.07 mm (0.328 in). The inner ampoule 48 was made of glass and was 3.96 cm (1.56 in) long, with an outer diameter of 6.5 mm (0.258 in) and a wall thickness of 2.5 mm (0.010 in). The closure member 52 was a 1.27 cm (0.5 in) diameter piece of "Monatec 5111-067," suture stock, commercially available from Monadnock Paper Mills, Inc., Bennington, N.H.

Assembly of Conventional Test Packs

The performance of six to eight unit batches of the above-described biological indicator devices was compared with conventional Association for the Advancement of Medical instrumentation (AAMI) steam test packs and with conventional biological indicators not contained in test packs. Each AAMI towel pack consisted of 16 freshly laundered "huck towels" commercially available from American Linen Supply Co., Minneapolis, Minn., in good condition, each of which was approximately 40.6×66 cm (16×26 inches). Each towel was folded lengthwise into thirds and folded widthwise in half. The towels were then placed on top of one another with folds opposite each other to form a stack approximately 23×23×15 cm (9×9×6 inches). Into each towel stack, four "Attest® 1262/1262P Biological Indicators" (Lot #057, Dec. 91) or four "Attest® 1291 Rapid Readout Biological Indicators" (Lot #085, Dec. 91) commercially available from 3M, St. Paul, Minn., were placed between the 8th and 9th towels from the bottom of the stack. The test packs were secured with autoclave tape.

Comparative Test

The devices of the invention and controls (consisting of a conventional Attest™ 1262/1262P Biological Indicator and a control biological indicator made as described above but without immobilization) not contained within AAMI test packs and placed within metal instrument trays, and the conventional AAMI biological test packs were exposed for 16, 18, 20, 22, and 24 minute intervals at a 121° C. (250° F.) gravity cycle (Table 1), and for 0, 1.5, 3.0 and 10.0 minute intervals at a 132° C. (270° F.) prevacuum cycle, 2 pulse, (Table 2), in a gravity displacement and vacuum assisted steam sterilizer, commercially available as an "Amsco Eagle™ Model 3000," from American Sterilizer Company, Erie, Pa. Following exposure, the conventional biological indicators were removed from the AAMI sixteen towel test pack. The inner ampoules of both the indicators of this invention and the conventional biological indicators were crushed and the units were incubated at 60° C. For the devices utilizing an enzyme substrate to indicate spore survival (i.e., all of the invention and the conventional test packs including the 1291 "Attest™ Biological Indicator (BI)"), an "Attest™ 190 Auto-Reader" commercially available from 3M, St. Paul, Minn., was used to fluorometrically read alpha-glucosidase activity by measuring 4-methylumbelliferyl fluorescence after 4 and 8 hours of incubation. Spore growth, as indicated by a color change produced by the pH indicator, was visually determined at 24, 48, and 168 hours of incubation for all units.

The results are reported in Tables 1 and 2. In the Tables of the Examples BI stands for "biological indicator".

TABLE 1

| | 121° C. (250° F.) Gravity Exposure - Number Positive/6 or 8 | | | | | | |
|---|---|---|---|---|---|---|---|
| | | Units Tested | Fluorescence | | Spore Outgrowth at | | |
| Sample | Immobilizer (W/V) | Exposure Time (min) | 4 hr | 8 hr | 24 hr | 48 hr | 168 hr |
| Attest ™ 1262/1262P BI | — | 16 | — | — | 6 | 6 | 6 |
| in AAMI Test Pack | | 18 | | | 4 | 4 | 4 |
| (8 units tested) | | 20 | | | 0 | 0 | 0 |
| | | 22 | | | 0 | 0 | 0 |
| | | 24 | | | 0 | 0 | 0 |
| Attest ™ 1291 Rapid | — | 16 | 8 | 8 | 8 | 8 | 8 |
| Readout BI in | | 18 | 4 | 4 | 4 | 4 | 4 |
| AAMI Test Pack | | 20 | 0 | 0 | 0 | 0 | 0 |
| (8 units tested) | | 22 | 0 | 0 | 0 | 0 | 0 |
| | | 24 | 0 | 0 | 0 | 0 | 0 |
| BI of Invention | D-sorbitol | 16 | 8 | 8 | 8 | 8 | 8 |
| (8 units tested) | (30%) | 18 | 7 | 7 | 0 | 0 | 0 |
| | | 20 | 4 | 4 | 0 | 0 | 0 |

TABLE 1-continued

121° C. (250° F.) Gravity Exposure - Number Positive/6 or 8

| Sample | Immobilizer (W/V) | Units Tested Exposure Time (min) | Fluorescence 4 hr | Fluorescence 8 hr | Spore Outgrowth at 24 hr | Spore Outgrowth at 48 hr | Spore Outgrowth at 168 hr |
|---|---|---|---|---|---|---|---|
|  |  | 22 | 0 | 0 | 0 | 0 | 0 |
|  |  | 24 | 0 | 0 | 0 | 0 | 0 |
| BI of Invention (8 units tested) | D-sorbitol (40%) | 16 | 8 | 8 | 8 | 8 | 8 |
|  |  | 18 | 8 | 8 | 3 | 3 | 3 |
|  |  | 20 | 8 | 8 | 0 | 0 | 0 |
|  |  | 22 | 8 | 8 | 0 | 0 | 0 |
|  |  | 24 | 0 | 0 | 0 | 0 | 0 |
| BI of Invention (6 units tested) | PEG-1450 (40%) | 16 | 6 | 6 | 6 | 6 | 6 |
|  |  | 18 | 6 | 6 | 5 | 6 | 6 |
|  |  | 20 | 1 | 1 | 1 | 1 | 1 |
|  |  | 22 | 0 | 0 | 0 | 0 | 0 |
|  |  | 24 | 0 | 0 | 0 | 0 | 0 |
| BI of Invention (6 units tested) | PEG-1450 (50%) | 16 | 6 | 6 | 6 | 6 | 6 |
|  |  | 18 | 6 | 6 | 6 | 6 | 6 |
|  |  | 20 | 5 | 5 | 5 | 5 | 5 |
|  |  | 22 | 1 | 1 | 0 | 0 | 0 |
|  |  | 24 | 0 | 0 | 0 | 0 | 0 |
| Attest ™ 1262/1262P BI Not contained in a test pack (6 units tested) | — | 16 | — | — | 0 | 0 | 0 |
|  |  | 18 |  |  | 0 | 0 | 0 |
|  |  | 20 |  |  | 0 | 0 | 0 |
|  |  | 22 |  |  | 0 | 0 | 0 |
|  |  | 24 |  |  | 0 | 0 | 0 |
| Control BI Not contained in a test pack (6 units tested) | — | 16 | — | — | 0 | 0 | 0 |
|  |  | 18 |  |  | 0 | 0 | 0 |
|  |  | 20 |  |  | 0 | 0 | 0 |
|  |  | 22 |  |  | 0 | 0 | 0 |
|  |  | 24 |  |  | 0 | 0 | 0 |

The symbol (—) indicates that no immobilizer was used or that readings were not taken.

TABLE 2

132° C. (270° F.) Gravity Exposure - Number Positive/6 or 8

| Sample | Immobilizer (W/V) | Units Tested Exposure Time (min) | Fluorescence 4 hr | Fluorescence 8 hr | Spore Outgrowth at 24 hr | Spore Outgrowth at 48 hr | Spore Outgrowth at 168 hr |
|---|---|---|---|---|---|---|---|
| Attest ™ 1262/1262P BI in AAMI Test Pack | — | 0 | — | — | 4 | 4 | 4 |
|  |  | 1.5 |  |  | 0 | 0 | 0 |
|  |  | 3.0 |  |  | 0 | 0 | 0 |
| Attest ™ 1291 Rapid Readout BI in AAMI Test Pack | — | 0 | 1 | 1 | 0 | 0 | 0 |
|  |  | 1.5 | 0 | 0 | 0 | 0 | 0 |
|  |  | 3.0 | 0 | 0 | 0 | 0 | 0 |
| BI of Invention | D-Sorbitol (30%) | 0 | 6 | 6 | 6 | 6 | 6 |
|  |  | 1.5 | 6 | 6 | 6 | 6 | 6 |
|  |  | 3.0 | 6 | 6 | 6 | 6 | 6 |
|  |  | 10.0 | 0 | 0 | 0 | 0 | 0 |
| BI of invention | D-Sorbitol (40%) | 0 | 6 | 6 | 6 | 6 | 6 |
|  |  | 1.5 | 6 | 6 | 6 | 6 | 6 |
|  |  | 3.0 | 6 | 6 | 5 | 5 | 5 |
|  |  | 10.0 | 0 | 0 | 0 | 0 | 0 |
| BI of Invention | PEG-1450 (40%) | 0 | 6 | 6 | 6 | 6 | 6 |
|  |  | 1.5 | 6 | 6 | 6 | 6 | 6 |
|  |  | 3.0 | 0 | 0 | 0 | 0 | 0 |
|  |  | 10.0 | 0 | 0 | 0 | 0 | 0 |
| BI of Invention | PEG-1450 (50%) | 0 | 6 | 6 | 6 | 6 | 6 |
|  |  | 1.5 | 6 | 6 | 6 | 6 | 6 |
|  |  | 3.0 | 0 | 0 | 0 | 0 | 0 |
|  |  | 10.0 | 0 | 0 | 0 | 0 | 0 |
| Attest ™ 1262/1262P BI Not contained in a test pack | — | 0 | — | — | 0 | 0 | 0 |
|  |  | 1.5 |  |  | 0 | 0 | 0 |
|  |  | 3.0 |  |  | 0 | 0 | 0 |
| Control BI Not contained in a Test Pack | — | 0 | — | — | 0 | 0 | 0 |
|  |  | 1.5 |  |  | 0 | 0 | 0 |
|  |  | 3.0 |  |  | 0 | 0 | 0 |

The symbol (—) indicates that no immobilizer was used or that readings were not taken.

The data presented above demonstrates that the biological indicators of the invention, utilizing spores and spore bound enzymes immobilized with D-sorbitol and polyethylene glycol can provide survival/kill and readout reliability results comparable with conventional biological indicators used in AAMI test packs. The biological indicators of the invention provide quick and convenient detection of sterilization efficacy, without the need to employ test pack materials or devices.

Example 2

This example illustrates that biological indicators of the invention utilizing immobilized alpha-glucosidase provide sterilization efficacy results comparable with conventional biological indicators in an AAMI sixteen towel test pack, at 121° C. (250° F.) gravity and 132° C. (270° F.) prevacuum sterilization exposures.

Preparation of Enzyme Strip

Lyophilized, purified alpha-glucosidase (Lot #001) derived from *Bacillus stearothermophilus* and with specific activity of 100 units/mg was obtained from Unitika Ltd., Kyoto, Japan. The alpha-glucosidase (0.1 g) was suspended in 1 ml of sterile distilled water. The enzyme suspension was dialyzed against 1 liter of sterile distilled water for 24 hours using "Spectra/Por® Molecularporous Membrane" commercially available from Spectrum Medical Industries Inc., Los Angeles, Calif., at a molecular weight limit of 3500 daltons. The dialyzed enzyme suspension was stored at 4° C. until needed. Dilutions of dialyzed alpha-glucosidase were made in sterile distilled water to give final concentrations of enzyme of 750 and 1500 units/ml. These dilutions of alpha-glucosidase were, coated and dried on 6.35×28.58 mm (¼×⅛ inch) strips of filter paper, commercially available as "S&S #903 Grade Filter Paper" from Schleicher & Schuell, Inc., Keene, N.H. This was accomplished by piperting 100 μl of each suspension onto each filter strip and allowing the strip to dry under ambient conditions.

Immobilization of Enzyme

The following method of immobilization of enzyme was employed. Strips of alpha-glucosidase were coated with the following aqueous chemical immobilizer solutions: "D-Sorbitol" commercially available from Pfizer, New York, N.Y., and polyethylene glycol commercially available as "Carbowax® PEG-1450" from Union Carbide Corporation, Danbury, Conn., at percent concentrations (w/v) specified in Tables 3 and 4 to obtain coating weights of approximately $2.75 \times 10^{-5}$ to $3.75 \times 10^{-5}$ g/square millimeter per individual strip. This was accomplished by pipetting 50 μl of the above solution of immobilizer compounds onto the enzyme coated strip. Immobilized enzyme strips were allowed to dry under ambient conditions for 24 hours, and devices were assembled.

Assembly of Devices

Devices were constructed utilizing the immobilized enzyme strip as illustrated in FIGS. 3 and 4, and described in Example 1.

Ten unit batches of the above-described biological indicator device (placed in metal instrument trays) and conventional biological indicators in Association for the Advancement of Medical Instrumentation (AAMI) steam test packs were exposed to a sterilization cycle as described in Example 1.

The devices of the invention and the conventional AAMI biological test packs were simultaneously exposed for 16, 18, and 20 minute intervals at a 121° C. (250° F.) gravity cycle (Table 1) and for 0, 1.5, and 3.0 minute intervals at a 132° C. (270° F.) prevacuum, 2 pulse cycle, (Table 2) in the sterilizer described in Example 1. After exposure, the conventional biological indicators were removed from the AAMI test packs, the inner ampoules of both the devices of the invention and the conventional biological indicators were crushed and the units were incubated at 60° C. Enzyme activity and spore growth were measured as described in Example 1. Spore growth could not be measured with the devices of the invention, since they utilized purified enzyme rather than spores to detect sterilization failure.

The results are reported in Tables 3 and 4.

TABLE 3

| | | | 121° C. (250° F.) Gravity Exposure - Number Positive/10 Units Tested | | | | | |
|---|---|---|---|---|---|---|---|---|
| | Immobilizer | Exposure | Fluorescence | | Spore Outgrowth at | | | |
| Sample | (W/V) | Time (min) | 4 hr | 8 hr | 24 hr | 48 hr | 168 hr | |
| Attest ™ 1262/1262P BI | — | 16 | — | — | 5 | 6 | 6 | |
| in AAMI Test Pack | | 18 | | | 0 | 0 | 0 | |
| | | 20 | | | 0 | 0 | 0 | |
| Attest ™ 1291 Rapid | — | 16 | 8 | 8 | 8 | 8 | 8 | |
| Readout BI in | | 18 | 0 | 0 | 0 | 0 | 0 | |
| AAMI Test Pack | | 20 | 0 | 0 | 0 | 0 | 0 | |
| BI of Invention | D-sorbitol | 16 | 10 | 10 | — | — | — | |
| (750 units/ml of | (30%) | 18 | 3 | 3 | | | | |
| alpha-glucosidase) | | 20 | 0 | 0 | | | | |
| BI of Invention | D-sorbitol | 16 | 10 | 10 | — | — | — | |
| (1500 units/ml of | | 18 | 10 | 10 | | | | |
| alpha-glucosidase) | (30%) | 20 | 0 | 0 | | | | |
| BI of Invention | PEG-1450 | 16 | 10 | 10 | — | — | — | |
| (750 units/ml of | (40%) | 18 | 0 | 0 | | | | |
| alpha-glucosidase) | | 20 | 0 | 0 | | | | |
| BI of Invention | PEG-1450 | 16 | 10 | 10 | — | — | — | |
| (1500 units/ml of | (50%) | 18 | 8 | 8 | | | | |
| alpha-glucosidase) | | 20 | 0 | 0 | | | | |

The symbol (—) indicates that no immobilizer was used or that those readings were not taken.

TABLE 4

132° C. (270° F.) Prevacuum Exposure - Number Positive/10 Units Tested

| Sample | Immobilizer (W/V) | Exposure Time (min) | Fluorescence 4 hr | Fluorescence 8 hr | Spore Outgrowth at 24 hr | 48 hr | 168 hr |
|---|---|---|---|---|---|---|---|
| Attest ™ 1262/1262P BI in AAMI Test Pack | — | 16 | — | — | 8 | 8 | 8 |
| | | 1.5 | | | 0 | 0 | 0 |
| | | 3.0 | | | 0 | 0 | 0 |
| Attest ™ 1291 Rapid Readout BI in AAMI Test Pack | — | 0 | 0 | 0 | 0 | 0 | 0 |
| | | 1.5 | 0 | 0 | 0 | 0 | 0 |
| | | 3.0 | 0 | 0 | 0 | 0 | 0 |
| BI of Invention (750 units/ml of alpha-glucosidase) | D-sorbitol (30%) | 0 | 10 | 10 | — | — | — |
| | | 1.5 | 2 | 2 | | | |
| | | 3.0 | 0 | 0 | | | |
| BI of Invention (1500 units/ml of alpha-glucosidase) | D-sorbitol (30%) | 0 | 10 | 10 | — | — | — |
| | | 1.5 | 9 | 9 | | | |
| | | 3.0 | 0 | 0 | | | |
| BI of Invention (750 units/ml of alpha-glucosidase) | PEG-1450 (40%) | 0 | 10 | 10 | — | — | — |
| | | 1.5 | 2 | 2 | | | |
| | | 3.0 | 0 | 0 | | | |
| BI of invention (1500 units/inl of alpha-glucosidase) | PEG-1450 (50%) | 0 | 10 | 10 | — | — | — |
| | | 1.5 | 10 | 10 | | | |
| | | 3.0 | 0 | 0 | | | |

The symbol (—) indicates that no immobilizer was used or that those readings were not taken.

The data presented above demonstrates that the biological indicators of the invention utilizing alpha-glucosidase immobilized with D-sorbitol and PEG-1450 can provide survival/kill readout comparable to conventional biological indicators used in AAMI test packs.

Example 3

This example illustrates the correlation between the biological indicators of this invention and conventional biological indicators in an AAMI sixteen towel test pack, to determine the efficacy of sterilization cycles of 121° C. (250° F.) gravity and 132° C. (270° F.) prevacuum.

*Bacillus stearothermophilus* commercially available as "ATCC 7953" from American Type Culture Collection, Rockville, Md., was grown as described in Example 1.

The *Bacillus stearothermophilus* spores were coated on filter paper dried, and immobilized as described in Example 1, except at a population of $1 \times 10^5$ spores per strip. This was accomplished by preparing a suspension of the spores in water at a concentration of $1 \times 10^7$ spores/ml, and pipetting 10 µl of this suspension onto each filter paper strip and allowing the strip to dry under ambient conditions.

Devices as illustrated in FIGS. 1 and 2 were constructed utilizing the immobilized spore strip as described in Example 1 except that the device contained no barrier 47.

Three unit batches of the devices containing immobilized *Bacillus stearothermophilus* spores and controls (Attest™ 1262/1262P and the control biological indicator made in accordance with Example 1) not contained within test packs and placed in metal instrument trays, and conventional biological indicators in AAMI steam test packs (prepared as described in Example 1) were exposed to steam sterilization cycles of 121° C. (250° F.) gravity (Table 5) and 132° C. (270° F.) prevacuum (Table 6) and evaluated for spore growth as described in Example 1.

The results are reported in Tables 5 and 6.

TABLE 5

121° C. (250° F.) Gravity Exposure - Number Positive/3 units Tested

| Sample | Immobilizer (W/V) | Exposure Time (min) | Spore Outgrowth at 24 hr | 48 hr | 168 hr |
|---|---|---|---|---|---|
| Attest ™ 1262/ 1262P BI in AAMI Test Pack | — | 16 | 3 | 3 | 3 |
| | | 18 | 1 | 1 | 1 |
| | | 20 | 0 | 0 | 0 |
| Attest ™ 1291 Rapid Readout BI in AAMI Test Pack | — | 16 | 3 | 3 | 3 |
| | | 18 | 0 | 0 | 0 |
| | | 20 | 0 | 0 | 0 |
| BI of Invention | D-sorbitol (30%) | 16 | 3 | 3 | 3 |
| | | 18 | 2 | 2 | 2 |
| | | 20 | 0 | 0 | 0 |
| BI of Invention | D-sorbitol (40%) | 16 | 3 | 3 | 3 |
| | | 18 | 3 | 3 | 3 |
| | | 20 | 0 | 0 | 0 |
| BI of Invention | PEG-1450 (40%) | 16 | 3 | 3 | 3 |
| | | 18 | 0 | 0 | 0 |
| | | 20 | 0 | 0 | 0 |
| BI of Invention | PEG-1450 (50%) | 16 | 3 | 3 | 3 |
| | | 18 | 2 | 2 | 2 |
| | | 20 | 0 | 0 | 0 |
| Attest ™ 1262/ 1262P BI Not Contained in a Test Pack | — | 16 | 0 | 0 | 0 |
| | | 18 | 0 | 0 | 0 |
| | | 20 | 0 | 0 | 0 |
| Control BI Not Contained in a Test Pack | — | 16 | 0 | 0 | 0 |
| | | 18 | 0 | 0 | 0 |
| | | 20 | 0 | 0 | 0 |

The symbol (—) indicates no immobilizer was used.

TABLE 6

132° C. (270° F.) Gravity Exposure - Number Positive/3 units Tested

| Sample | Immobilizer (W/V) | Exposure Time (min) | Spore Outgrowth at 24 hr | 48 hr | 168 hr |
|---|---|---|---|---|---|
| Attest ™ 1262/ 1262P BI in AAMI Test Pack | — | 0 | 3 | 3 | 3 |
| | | 1.5 | 1 | 1 | 1 |
| | | 3.0 | 0 | 0 | 0 |

TABLE 6-continued

132° C. (270° F.) Gravity Exposure - Number Positive/3 units Tested

| Sample | Immobilizer (W/V) | Exposure Time (min) | Spore Outgrowth at | | |
|---|---|---|---|---|---|
| | | | 24 hr | 48 hr | 168 hr |
| Attest ™ 1291 | — | 0 | 0 | 0 | 0 |
| Rapid Readout BI | | 1.5 | 0 | 0 | 0 |
| in AAMI Test Pack | | 3.0 | 0 | 0 | 0 |
| BI of Invention | D-sorbitol | 0 | 3 | 3 | 3 |
| | (30%) | 1.5 | 3 | 3 | 3 |
| | | 3.0 | 1 | 1 | 1 |
| | | 10.0 | 0 | 0 | 0 |
| BI of Invention | D-sorbitol | 0 | 3 | 3 | 3 |
| | (40%) | 1.5 | 3 | 3 | 3 |
| | | 3.0 | 3 | 3 | 3 |
| | | 10.0 | 0 | 0 | 0 |
| BI of Invention | PEG-1450 | 0 | 3 | 3 | 3 |
| | (40%) | 1.5 | 3 | 3 | 3 |
| | | 3.0 | 3 | 3 | 3 |
| | | 10.0 | 0 | 0 | 0 |
| BI of Invention | PEG-1450 | 0 | 3 | 3 | 3 |
| | (50%) | 1.5 | 3 | 3 | 3 |
| | | 3.0 | 3 | 3 | 3 |
| | | 10.0 | 0 | 0 | 6 |
| Attest ™ 1262/ | — | 0 | 0 | 0 | 0 |
| 1262P BI Not | | 1.5 | 0 | 0 | 0 |
| Contained in Test | | 3.0 | 0 | 0 | 0 |
| Pack | | 10.0 | 0 | 0 | 0 |
| Control BI Not | — | 0 | 0 | 0 | 0 |
| Contained in Test | | 1.5 | 0 | 0 | 0 |
| Pack | | 3.0 | 0 | 0 | 0 |
| | | 10.0 | 0 | 0 | 0 |

The devices of this invention were designed to provide microbial challenge during exposure to 121° C. (250° F.) gravity and 132° C. (270° F.) prevacuum steam cycles which is equal to or greater than the microbial challenge provided by the AAMI biological indicator test packs. The data presented above demonstrates that the invention utilizing D-sorbitol and PEG-1450 immobilized spores achieves and out-performs these requirements.

Example 4

This example illustrates the use of various concentrations of immobilized *Bacillus stearothermophilus* spores useful in the practice of this invention.

*Bacillus stearothermophilus* commercially available as "ATCC 7953" from American Type Culture Collection were grown as described in Example 1.

The *Bacillus stearothermophilus* spores were coated, dried, and immobilized as described in Example 1 except at a population of $1.0 \times 10^2$ and $1.0 \times 10^4$ spores per strip.

Devices were constructed as illustrated in FIGS. 1 and 2.

Three unit batches of the invention described above (placed in metal instruments trays) and conventional AAMI biological indicator steam test packs (as described in Example 1) were simultaneously exposed for 15, 18, 21, 24, 27 and 30 minutes to a 121° C. (250° F.) gravity steam sterilization cycle as described in Example 1. The inner ampoules of the devices were crushed and the units were incubated at 56° C. Spore growth was measured as described in Example 1.

The results are reported in Table 7.

TABLE 7

121° C. (250° F.) Gravity Exposure - Number Positive/3 Units Tested

| Sample | Immobilizer (W/V) | Exposure Time (min) | Spore Outgrowth at | | |
|---|---|---|---|---|---|
| | | | 24 hr | 48 hr | 168 hr |
| Attest ™ 1262/ | — | 15 | 3 | 3 | 3 |
| 1262P BI in AAMI | | 18 | 2 | 2 | 2 |
| Test Pack | | 21 | 0 | 0 | 0 |
| | | 24 | 0 | 0 | 0 |
| | | 27 | 0 | 0 | 0 |
| | | 30 | 0 | 0 | 0 |
| BI of Invention | D-sorbitol | 15 | 3 | 3 | 3 |
| ($1 \times 10^2$ spores per strip) | (40%) | 18 | 2 | 2 | 2 |
| | | 21 | 1 | 1 | 1 |
| | | 24 | 0 | 0 | 0 |
| | | 27 | 0 | 0 | 0 |
| | | 30 | 0 | 0 | 0 |
| BI of Invention | D-sorbitol | 15 | 3 | 3 | 3 |
| ($1 \times 10^2$ spores per strip) | (50%) | 18 | 3 | 3 | 3 |
| | | 21 | 3 | 3 | 3 |
| | | 24 | 0 | 0 | 0 |
| | | 27 | 0 | 0 | 0 |
| | | 30 | 0 | 0 | 0 |
| BI of Invention | PEG-1450 | 15 | 3 | 3 | 3 |
| ($1 \times 10^2$ spores per strip) | (50%) | 18 | 2 | 2 | 2 |
| | | 21 | 0 | 0 | 0 |
| | | 24 | 0 | 0 | 0 |
| | | 27 | 0 | 0 | 0 |
| | | 30 | 0 | 0 | 0 |
| BI of Invention | PEG-1450 | 15 | 3 | 3 | 3 |
| ($1 \times 10^2$ spores per strip) | (60%) | 18 | 3 | 3 | 3 |
| | | 21 | 0 | 0 | 0 |
| | | 24 | 0 | 0 | 0 |
| | | 27 | 0 | 0 | 0 |
| | | 30 | 0 | 0 | 0 |
| BI of Invention | D-sorbitol | 15 | 3 | 3 | 3 |
| ($1 \times 10^4$ spores per strip) | (40%) | 18 | 3 | 3 | 3 |
| | | 21 | 1 | 1 | 1 |
| | | 24 | 0 | 0 | 0 |
| | | 27 | 0 | 0 | 0 |
| | | 30 | 0 | 0 | 0 |
| BI of Invention | D-sorbitol | 15 | 3 | 3 | 3 |
| ($1 \times 10^4$ spores per strip) | (50%) | 18 | 3 | 3 | 3 |
| | | 21 | 3 | 3 | 3 |
| | | 24 | 1 | 1 | 1 |
| | | 27 | 0 | 0 | 0 |
| | | 30 | 0 | 0 | 0 |
| BI of Invention | PEG-1450 | 15 | 3 | 3 | 3 |
| ($1 \times 10^4$ spores per strip) | (50%) | 18 | 3 | 3 | 3 |
| | | 21 | 3 | 3 | 3 |
| | | 24 | 0 | 0 | 0 |
| | | 27 | 0 | 0 | 0 |
| | | 30 | 0 | 0 | 0 |
| BI of Invention | PEG-1450 | 15 | 3 | 3 | 3 |
| ($1 \times 10^4$ spores per strip) | (60%) | 18 | 3 | 3 | 3 |
| | | 21 | 3 | 3 | 3 |
| | | 24 | 3 | 3 | 3 |
| | | 27 | 0 | 0 | 0 |
| | | 30 | 0 | 0 | 0 |

The data presented above demonstrates that the invention utilizing D-sorbitol and PEG1450 immobilized spores at various concentrations of spores per strip achieved and sometimes exceeded the performance of the conventional AAMI biological indicator test pack.

Example 5

This example illustrates the use of different strains of immobilized *Bacillus stearothermophilus* spores useful in the practice of this invention.

The following strains were tested: "ATCC 8005" and "ATCC 12980", commercially available from American Type Culture Collection, Rockville, Md.; "NCTC 10003", commercially available from Nation Collection of Type Cultures, Colindale, London, England; "German Earthspore" obtained by culturing earth strips supplied by the Hygiene Institute of Hamburg, Germany; and Scandinavian strain isolated from spore strips produced by Staten Institute for Falkehelse, Oslo, Norway.

All spores were grown on a nutrient agar medium as described in Example 1. The spores were centrifuged at 11,000 rpm for 5 hours at 4° C. in density gradients commercially available as "Percoil®" from Pharmacia Fine Chemicals AB, Uppsala, Sweden. After centrifuging, the spores were resuspended in sterile distilled water. With the German Earthspore strain, two distinct layers of cells were isolated in the density gradient during centrifugation. Using phase contact microscopy, the bottom layer was predominately spores and the top layer was predominately vegetative cells. The spore layer was utilized for this example.

The Bacillus stearothermophilus spores were coated at a population of $1 \times 10^6$ spores per strip, dried, and immobilized as described in Example 1.

Devices were constructed as illustrated in FIGS. 1 and 2 and described in Example 3.

Three unit batches of the devices described above (placed in metal instrument trays) and with conventional biological indicators in AAMI steam test packs (constructed as described in Example 1) were simultaneously exposed for 15, 18, 21, 24, 27 and 30 minutes in a 121° C. (250° F.) gravity steam sterilization cycle as described in Example 1. The inner ampoules of the devices were crushed, and the units incubated at 56° C. Spore growth was measured as described in Example 1.

TABLE 8

| | | | Spore Outgrowth at | | |
|---|---|---|---|---|---|
| Sample | Immobilizer (W/V) | Exposure Time (min) | 24 hr | 48 hr | 168 hr |
| Attest ™ 1262/ 1262P BI in AAMI Test Pack | — | 15 | 3 | 3 | 3 |
| | | 18 | 0 | 0 | 0 |
| | | 21 | 0 | 0 | 0 |
| | | 24 | 0 | 0 | 0 |
| | | 27 | 0 | 0 | 0 |
| | | 30 | 0 | 0 | 0 |
| BI of Invention (using ATCC 8005) | D-sorbitol (40%) | 15 | 3 | 3 | 3 |
| | | 18 | 3 | 3 | 3 |
| | | 21 | 0 | 0 | 0 |
| | | 24 | 0 | 0 | 0 |
| | | 27 | 0 | 0 | 0 |
| | | 30 | 0 | 0 | 0 |
| BI of Invention (using NCTC 10003) | D-sorbitol (50%) | 15 | 3 | 3 | 3 |
| | | 18 | 2 | 2 | 2 |
| | | 21 | 0 | 0 | 0 |

121° C. (250° F.) Gravity Exposure - Number Positive/3 Units Tested

TABLE 8-continued

121° C. (250° F.) Gravity Exposure - Number Positive/3 Units Tested

| | | | Spore Outgrowth at | | |
|---|---|---|---|---|---|
| Sample | Immobilizer (W/V) | Exposure Time (min) | 24 hr | 48 hr | 168 hr |
| | | 24 | 0 | 0 | 0 |
| | | 27 | 0 | 0 | 0 |
| | | 30 | 0 | 0 | 0 |
| BI of Invention (using Scandinavian strain) | D-sorbitol (50%) | 15 | 3 | 3 | 3 |
| | | 18 | 3 | 3 | 3 |
| | | 21 | 0 | 0 | 0 |
| | | 24 | 0 | 0 | 0 |
| | | 27 | 0 | 0 | 0 |
| | | 30 | 0 | 0 | 0 |
| BI of Invention (using German Earthspore) | D-sorbitol (50%) | 15 | 3 | 3 | 3 |
| | | 18 | 0 | 0 | 0 |
| | | 21 | 0 | 0 | 0 |
| | | 24 | 0 | 0 | 0 |
| | | 27 | 0 | 0 | 0 |
| | | 30 | 0 | 0 | 0 |

The data presented above demonstrates that the invention utilizing various different strains of B-stearothermophilus spores immobilized with D-sorbitol achieved and sometimes exceeded the performance requirements of the AAMI biological indicator test pack at 121° C. (250° F.) gravity exposures.

Example 6

This example illustrates the effect of various concentrations of the immobilizing agents, D-sorbitol and PEG-1450, on survival/kill times for Bacillus stearothermophilus ATCC 7953 immobilized spores and spore bound enzyme at 121° C. (250° F.) gravity exposures.

All spores were grown on nutrient agar medium as described in Example 1.

The Bacillus stearothermophilus spores were coated, dried, and immobilized as described in Example 1.

Devices were constructed as illustrated in FIGS. 3 and 4 and described in Example 1.

Three unit batches of the devices described above and the biological indicator control made in accordance with Example 1 were placed in metal instruments trays and exposed for 10, 11, 12, 13, 14, 15, 16, 17, 18, 19, 20, 21, 22, 23, 24, and 25 minutes in a 121° C. (250° F.) gravity steam sterilization cycle as described in Example 1. The inner ampoules of the devices were crushed, and the units incubated at 60° C. Enzyme activity and spore growth were evaluated as described in Example 1. Enzyme activity is reported in Table 9 and spore growth is reported in Table 10.

TABLE 9

121° C. (250° F.) Gravity Exposure - Number Positive/3 Units Tested

| | | Fluorescence after 4 hours Exposure Time (min) | | | | | | | | | | | | | |
|---|---|---|---|---|---|---|---|---|---|---|---|---|---|---|---|
| Immobilizer | (W/V) | 10 | 11 | 12 | 13 | 14 | 15 | 16 | 17 | 18 | 19 | 20 | 21 | 22 | 23 | 24 |
| D-Sorbitol | (10%) | 3 | 3 | 3 | 3 | 3 | 3 | 3 | 3 | 2 | 0 | 0 | 0 | 0 | 0 | 0 |
| D-Sorbitol | (20%) | 3 | 3 | 3 | 3 | 3 | 3 | 3 | 3 | 3 | 3 | 0 | 0 | 0 | 0 | 0 |
| D-Sorbitol | (30%) | 3 | 3 | 3 | 3 | 3 | 3 | 3 | 3 | 3 | 3 | 3 | 0 | 0 | 0 | 0 |
| D-Sorbitol | (40%) | 3 | 3 | 3 | 3 | 3 | 3 | 3 | 3 | 3 | 3 | 3 | 3 | 2 | 0 | 0 |
| D-Sorbitol | (50%) | 3 | 3 | 3 | 3 | 3 | 3 | 3 | 3 | 3 | 3 | 3 | 3 | 3 | 0 | 0 |

TABLE 9-continued

121° C. (250° F.) Gravity Exposure - Number Positive/3 Units Tested

| | | Fluorescence after 4 hours Exposure Time (min) | | | | | | | | | | | | | |
|---|---|---|---|---|---|---|---|---|---|---|---|---|---|---|---|
| Immobilizer | (W/V) | 10 | 11 | 12 | 13 | 14 | 15 | 16 | 17 | 18 | 19 | 20 | 21 | 22 | 23 | 24 |
| PEG-1450 | (10%) | 3 | 3 | 3 | 3 | 3 | 3 | 0 | 0 | 0 | 0 | 0 | 0 | 0 | 0 | 0 |
| PEG-1450 | (20%) | 3 | 3 | 3 | 3 | 3 | 3 | 3 | 0 | 0 | 0 | 0 | 0 | 0 | 0 | 0 |
| PEG-1450 | (30%) | 3 | 3 | 3 | 3 | 3 | 3 | 3 | 3 | 2 | 0 | 0 | 0 | 0 | 0 | 0 |
| PEG-1450 | (40%) | 3 | 3 | 3 | 3 | 3 | 3 | 3 | 3 | 3 | 3 | 0 | 0 | 0 | 0 | 0 |
| PEG-1450 | (50%) | 3 | 3 | 3 | 3 | 3 | 3 | 3 | 3 | 3 | 3 | 3 | 1 | 0 | 0 | 0 |
| Control | (6%) | 0 | 0 | 0 | 0 | 0 | 0 | 0 | 0 | 0 | 0 | 0 | 0 | 0 | 0 | 0 |

TABLE 10

121° C. (250° F.) Gravity Exposure - Number Positive/3 Units Tested

| | | Growth after 4 hours Exposure Time (min) | | | | | | | | | | | | | |
|---|---|---|---|---|---|---|---|---|---|---|---|---|---|---|---|
| Immobilizer | (W/V) | 10 | 11 | 12 | 13 | 14 | 15 | 16 | 17 | 18 | 19 | 20 | 21 | 22 | 23 | 24 |
| D-Sorbitol | (10%) | 3 | 3 | 3 | 3 | 3 | 0 | 0 | 0 | 0 | 0 | 0 | 0 | 0 | 0 | 0 |
| D-Sorbitol | (20%) | 3 | 3 | 3 | 3 | 3 | 3 | 1 | 0 | 0 | 0 | 0 | 0 | 0 | 0 | 0 |
| D-Sorbitol | (30%) | 3 | 3 | 3 | 3 | 3 | 3 | 3 | 0 | 0 | 0 | 0 | 0 | 0 | 0 | 0 |
| D-Sorbitol | (40%) | 3 | 3 | 3 | 3 | 3 | 3 | 3 | 3 | 3 | 0 | 0 | 0 | 0 | 0 | 0 |
| D-Sorbitol | (50%) | 3 | 3 | 3 | 3 | 3 | 3 | 3 | 3 | 3 | 2 | 0 | 0 | 0 | 0 | 0 |
| PEG-1450 | (10%) | 3 | 3 | 3 | 3 | 3 | 2 | 0 | 0 | 0 | 0 | 0 | 0 | 0 | 0 | 0 |
| PEG-1450 | (20%) | 3 | 3 | 3 | 3 | 3 | 3 | 3 | 0 | 0 | 0 | 0 | 0 | 0 | 0 | 0 |
| PEG-1450 | (30%) | 3 | 3 | 3 | 3 | 3 | 3 | 3 | 3 | 3 | 0 | 0 | 0 | 0 | 0 | 0 |
| PEG-1450 | (40%) | 3 | 3 | 3 | 3 | 3 | 3 | 3 | 3 | 3 | 3 | 1 | 0 | 0 | 0 | 0 |
| PEG-1450 | (50%) | 3 | 3 | 3 | 3 | 3 | 3 | 3 | 3 | 3 | 3 | 3 | 0 | 0 | 0 | 0 |
| Control | (0%) | 0 | 0 | 0 | 0 | 0 | 0 | 0 | 0 | 0 | 0 | 0 | 0 | 0 | 0 | 0 |

The data presented above demonstrates that immobilization of spores and spore bound enzymes with increasing concentrations of D-sorbitol and PEG-1450 increases the exposure time required to kill the spores and destroy enzyme on the spore strip.

Example 7

This example illustrates the use of D-sorbitol to enhance the survival/kill performance of the spore bound enzyme and spore when used in conventional test packs (as shown in FIG. 5) at 132° C. (270° F.) prevacuum exposure.

All spores were grown on nutrient agar medium as described in Example 1.

Suspensions of *Bacillus stearothermophilus* spores and D-sorbitol in water at the percent weight concentrations indicated in Table 11 were made. This was accomplished by suspending washed *Bacillus stearothermophilus* spores at a concentration of $7.5 \times 10^7$ spores/ml into 10% and 20% w/v suspensions of D-sorbitol. The suspensions were mixed, coated, and dried on 6.35×9.52 mm (¼×⅜ inch) strips of filter paper, commercially available as "S&S #903 Grade Filter Paper" from Schleicher & Schuell, Inc., Keene, N.H., at a population of $7.5 \times 10^5$ spores per strip. This was accomplished by pipetting 10 μl of suspension onto each filter strip and allowing the strip to dry under ambient conditions.

Devices were constructed as illustrated in FIGS. 3 and 4 and described in Example 1.

Three unit batches of the devices described above and conventional biological indicators ("Attest™ Rapid Readout Biological Indicator 1291" (Lot #085, December 1991)) were placed into "Attest™ 1276 test packs," commercially available from 3M, St. Paul, Minn.

The test packs utilizing the biological indicators of the invention and the conventional biological indicator packs were exposed for 0.5, 1, and 4 minute intervals to a 132° C. (270° F.) prevacuum steam sterilization cycle, 2 pulse, as described in Example 1. The biological indicators were removed from the test packs, the inner ampoules were crushed, and each unit was incubated at 60° C. Enzyme activity and spore growth were evaluated as described in Example 1. The results are reported in Table 11.

TABLE 11

132° C. (270° F.) Prevacuum Exposure - Number Positive/3 Units Tested

| Sample (in Attest™ 1276 Test Pack) | Immobilizer (W/V) | Exposure Time (min) | Fluorescence | | Spore outgrowth at | | |
|---|---|---|---|---|---|---|---|
| | | | 4 hr | 8 hr | 24 hr | 48 hr | 168 hr |
| 1291 Attest™ BI | — | 0.5 | 0 | 0 | 0 | 0 | 0 |
| | | 1.0 | 0 | 0 | 0 | 0 | 0 |
| | | 4.0 | 0 | 0 | 0 | 0 | 0 |
| BI of Invention | D-sorbitol (10%) | 0.5 | 3 | 3 | 3 | 3 | 3 |
| | | 1.0 | 3 | 3 | 3 | 3 | 3 |
| | | 4.0 | 0 | 0 | 0 | 0 | 0 |
| BI of Invention | D-sorbitol (20%) | 0.5 | 3 | 3 | 3 | 3 | 3 |
| | | 1.0 | 3 | 3 | 2 | 3 | 3 |
| | | 4.0 | 0 | 0 | 0 | 0 | 0 |

The data presented above demonstrates that *Bacillus stearothermophilus* spores and spore bound enzyme, alpha-glucosidase, immobilized with relatively low concentrations of D-sorbitol can increase the survival time for spores in conventional test packs to exceed the performance of conventional biological indicators in those test packs. Increased spore survival time improves the performance of the test pack because a greater portion of the sterilization cycle can be monitored.

Example 8

This example illustrates the use of other immobilizing compounds to immobilize *Bacillus stearothermophilus* spores. The following list of compounds (and sources) were utilized:

"myo-erythritol," Sigma® Chemical Co., St. Louis, Mo.
"adonitol," Sigma® Chemical Co.
"dulcitol," Sigma® Chemical Co.
"D-mannitol," Sigma® Chemical Co.
"xylitol," Sigma® Chemical Co.
"D-arabinitol," Sigma® Chemical Co.
"D(+)-cellobiose," Sigma® Chemical Co.
"sucrose," Sigma® Chemical Co.
"meso-inositol," Sigma® Chemical Co.
"glycerol," Aldrich Chem. Co., Inc., Milwaukee, Wis.
"polyvinylalcohol (PVA)," Aldrich Chem. Co., Inc.
"trehalose," Sigma® Chemical Co.
"lactose," Sigma® Chemical Co.
"raffinose," Sigma® Chemical Co.
"melezitose," Sigma® Chemical Co.
"maltose," Sigma® Chemical Co.

Bacillus stearothermophilus commercially available as "ATCC 7953" were grown as described in Example 1.

The *Bacillus stearothermophilus* spores were coated at a population of $1 \times 10^5$ spores per strip, dried, and immobilized as described in Example 1 with one of the chemical immobilizers listed above.

Devices were constructed utilizing the immobilized spore strip as illustrated in FIGS. 1 and 2 and described in Example 3.

Three unit batches of the devices described above (placed in metal instrument trays) and conventional biological indicators in AAMI steam test packs described in Example 1) were simultaneously exposed for 15, 18, 21, 24, 27, and 30 minute intervals to a 121° C. (250° F.) gravity steam sterilization cycle as described in Example 1. The inner ampoules of the biological indicators were crushed, and the units incubated at 56° C. Spore growth was evaluated as described in Example 1, and the results are reported in Table 12.

TABLE 12

121° C. (250° F.) Gravity Exposure - Number Positive/3 Units Tested

| Sample | Immobilizer (W/V) | Exposure Time (min) | Spore Outgrowth at | | |
|---|---|---|---|---|---|
| | | | 24 hr | 48 hr | 168 hr |
| Attest™ 1262/ 1262P BI in in AAMI Test Pack | — | 15 | 3 | 3 | 3 |
| | | 18 | 2 | 2 | 2 |
| | | 21 | 0 | 0 | 0 |
| | | 24 | 0 | 0 | 0 |
| | | 27 | 0 | 0 | 0 |
| | | 30 | 0 | 0 | 0 |
| Attest™ 1262/ 1262P BI Not Contained in Test Pack | — | 15 | 0 | 0 | 0 |
| | | 18 | 0 | 0 | 0 |
| | | 21 | 0 | 0 | 0 |
| | | 24 | 0 | 0 | 0 |
| | | 27 | 0 | 0 | 0 |
| | | 30 | 0 | 0 | 0 |
| BI of Invention | PVA (0.75%) | 15 | 3 | 3 | 3 |
| | | 18 | 0 | 0 | 0 |
| | | 21 | 0 | 0 | 0 |
| | | 24 | 0 | 0 | 0 |
| | | 27 | 0 | 0 | 0 |
| | | 30 | 0 | 0 | 0 |
| BI of Invention | Adonitol (30%) | 15 | 3 | 3 | 3 |
| | | 18 | 0 | 0 | 0 |
| | | 21 | 0 | 0 | 0 |
| | | 24 | 0 | 0 | 0 |
| | | 27 | 0 | 0 | 0 |
| | | 30 | 0 | 0 | 0 |
| BI of Invention | Xylitol (40%) | 15 | 3 | 3 | 3 |
| | | 18 | 3 | 3 | 3 |
| | | 21 | 0 | 0 | 0 |
| | | 24 | 0 | 0 | 0 |
| | | 27 | 0 | 0 | 0 |
| | | 30 | 0 | 0 | 0 |
| BI of Invention | Myo-erythritol (40%) | 15 | 2 | 2 | 2 |
| | | 18 | 1 | 2 | 2 |
| | | 21 | 0 | 0 | 0 |
| | | 24 | 0 | 0 | 0 |
| | | 27 | 0 | 0 | 0 |
| | | 30 | 0 | 0 | 0 |
| BI of Invention | Glycerin (40%) | 15 | 3 | 3 | 3 |
| | | 18 | 2 | 3 | 3 |
| | | 21 | 1 | 1 | 1 |
| | | 24 | 0 | 0 | 0 |
| | | 27 | 0 | 0 | 0 |
| | | 30 | 0 | 0 | 0 |
| BI of Invention | Maltose (50%) | 15 | 1 | 2 | 2 |
| | | 18 | 0 | 0 | 0 |
| | | 21 | 0 | 0 | 0 |
| | | 24 | 0 | 0 | 0 |
| | | 27 | 0 | 0 | 0 |
| | | 30 | 0 | 0 | 0 |

TABLE 12-continued

121° C. (250° F.) Gravity Exposure - Number Positive/3 Units Tested

| Sample | Immobilizer (W/V) | Time (min) | Exposure Spore Outgrowth at | | |
|---|---|---|---|---|---|
| | | | 24 hr | 48 hr | 168 hr |
| BI of Invention | D-Mannitol (30%) | 15 | 3 | 3 | 3 |
| | | 18 | 3 | 3 | 3 |
| | | 21 | 2 | 2 | 2 |
| | | 24 | 0 | 0 | 0 |
| | | 27 | 0 | 0 | 0 |
| | | 30 | 0 | 0 | 0 |
| BI of Invention | Myo-inositol (20%) | 15 | 3 | 3 | 3 |
| | | 18 | 3 | 3 | 3 |
| | | 21 | 2 | 2 | 2 |
| | | 24 | 0 | 0 | 0 |
| | | 27 | 0 | 0 | 0 |
| | | 30 | 0 | 0 | 0 |
| BI of Invention | Dulcitol (10%) | 15 | 3 | 3 | 3 |
| | | 18 | 2 | 2 | 2 |
| | | 21 | 0 | 0 | 0 |
| | | 24 | 0 | 0 | 0 |
| | | 27 | 0 | 0 | 0 |
| | | 30 | 0 | 0 | 0 |
| BI of Invention | D(+)-Cellobiose (30%) | 15 | 3 | 3 | 3 |
| | | 18 | 3 | 3 | 3 |
| | | 21 | 1 | 1 | 1 |
| | | 24 | 0 | 0 | 0 |
| | | 27 | 0 | 0 | 0 |
| | | 30 | 0 | 0 | 0 |
| BI of Invention | D-arabinitol (20%) | 15 | 3 | 3 | 3 |
| | | 18 | 0 | 2 | 2 |
| | | 21 | 0 | 0 | 0 |
| | | 24 | 0 | 0 | 0 |
| | | 27 | 0 | 0 | 0 |
| | | 30 | 0 | 0 | 0 |
| BI of Invention | Sucrose (40%) | 15 | 3 | 3 | 3 |
| | | 18 | 3 | 3 | 3 |
| | | 21 | 0 | 0 | 0 |
| | | 24 | 0 | 0 | 0 |
| | | 27 | 0 | 0 | 0 |
| | | 30 | 0 | 0 | 0 |
| BI of Invention | Trehalose (50%) | 15 | 3 | 3 | 3 |
| | | 18 | 1 | 2 | 2 |
| | | 21 | 0 | 0 | 0 |
| | | 24 | 0 | 0 | 0 |
| | | 27 | 0 | 0 | 0 |
| | | 30 | 0 | 0 | 0 |
| BI of Invention | Lactose (60%) | 15 | 3 | 3 | 3 |
| | | 18 | 0 | 0 | 0 |
| | | 21 | 0 | 0 | 0 |
| | | 24 | 0 | 0 | 0 |
| | | 27 | 0 | 0 | 0 |
| | | 30 | 0 | 0 | 0 |
| BI of Invention | Raffinose (50%) | 15 | 3 | 3 | 3 |
| | | 18 | 0 | 2 | 2 |
| | | 21 | 0 | 2 | 2 |
| | | 24 | 0 | 0 | 0 |
| | | 27 | 0 | 0 | 0 |
| | | 30 | 0 | 0 | 0 |
| BI of Invention | Melezitose (40%) | 15 | 2 | 3 | 3 |
| | | 18 | 1 | 3 | 3 |
| | | 21 | 0 | 1 | 1 |
| | | 24 | 0 | 0 | 0 |
| | | 27 | 0 | 0 | 0 |
| | | 30 | 0 | 0 | 0 |

The data presented above demonstrates the use of a variety of immobilizing compounds to provide biological indicators which have survival/kill time points and readout reliability comparable to conventional biological indicators utilizing test packs.

Example 9

This example illustrates several enzymes, associated with *Bacillus stearothermophilus*, which are useful in the practice of the present invention. In this example an enzyme substrate kit, commercially available as "API-XYM™ System" from API Analytab Products, Plainview, N.Y., was utilized. This kit consisted of 19 different dehydrated, chromogenic enzymatic substrates, packed individually in a series of microcupules. The addition of an aqueous sample to each microcupule rehydrates the substrate. The test kit was incubated for a desired time interval and the reactions were visually read after the addition of the detector reagents supplied with the system.

*Bacillus stearothermophilus* spores "ATCC 7953" were grown as described in Example 1.

The *Bacillus stearothermoohilus* spores were coated and dried on strips of filter paper as described in Example 1 at a population of $1\times10^5$ spores per strip. This was accomplished by preparing a suspension of the spores in water at a concentration of $1\times10^5$ spores/ml, and pipetting 10 µl of this suspension on each filter strip and allowing the strip to dry under ambient conditions. The spores were immobilized as described in Example 1 using "D-Sorbitol" at a percent concentration of 30 percent, weight to volume.

Devices were constructed using the spore strips as illustrated in FIGS. 3 and 4 and described in Example 1.

Three unit batches of the device of the invention were exposed for 15 and 30 minutes at a 121° C. (250° F.) gravity cycle in the sterilizer as described in Example 1. Following exposure, the spore strips were aseptically removed and transferred to each microcupule in the enzyme substrate kit and 100 µl of sterile tryptic soy broth was added to each well. One kit contained the immobilized spore strips exposed for 15 minutes, a second kit contained the immobilized spore strips exposed for 30 minutes, and the third kit contained unexposed immobilized spore strips.

The kits were incubated at 56° C. for 7.5 hours. After incubation, the detector reagents A and B, available with the API-XYM™ system were added for substrate development. The detection of color in each microcapsule indicates the pressence of active enzymes. Results are reported in Table 13.

TABLE 13

| | Spore Strip Exposure | | |
|---|---|---|---|
| Enzyme Assayed for | 0 Minutes | 15 Minutes | 30 Minutes |
| Alkaline phosphatase | 3 | 3 | 0 |
| Butyrate esterase | 4 | 5 | 0 |
| Caprylate esterase lipase | 3 | 3 | 0 |
| Myristate lipase | 1 | 1 | 0 |
| Leucine aminopeptidase | 2 | 3 | 0 |
| Valine aminopeptidase | 1 | 1 | 0 |
| Cystine aminopeptidase | 0 | 0 | 0 |
| Trypsin | 0 | 0 | 0 |
| Chymotrypsin | 2 | 2 | 0 |
| Acid phosphatase | 3 | 3 | 0 |
| Phosphohydrolase | 4 | 4 | 0 |
| Alpha-galactosidase | 4 | 5 | 0 |
| Beta-galactosidase | 0 | 0 | 0 |
| Beta-glucuronidase | 1 | 1 | 0 |
| Alpha-glucosidase | 4 | 4 | 0 |
| Beta-glucosidase- | 3 | 4 | 0 |
| N-acetyl-beta-glucosaminidase | 0 | 0 | 0 |
| Alpha-mannosidase | 0 | 0 | 0 |
| Alpha-fucosidase | 0 | 0 | 0 |

* 0 = no color developemnt
1 = Weak development
2, 3, 4 = Intermediate color development increasing with number
5 = Strong color development The data presented above demonstrates a number of enzymes indigenous to *Bacillus stearothermophilus* spores which have sufficient activity to be useful in the practice of the invention. All of the enzymes evaluated which were indigenous to *Bacillus stearothermophilus* showed detectable activity after an ineffective sterilization cycle of 15 minutes, but no activity after exposure for 30 minutes. Several enzymes are not indigenous to *Bacillus stearothermophilus* and displayed no activity in the exposed or unexposed state.

Example 10

This example illustrates the use of various chemicals to immobilize *Bacillus subtilis* spores. The following immobilizer compounds (listed with their sources) were utilized:

"myo-erythritol," Sigma® Chemical Co., St. Louis, MO
"adonitol," Sigma
"dulcitol," Sigma
"D-mannitol," Sigma
"xylitol," Sigma
"polyol-P," Pfizer, New York, N.Y.
"D-arabinitol," Sigma
"D(+)-cellobiose," Sigma
"sucrose," Sigma
"myo-inositol," Sigma
"glycerol," Aldrich Chemical Co., Inc., Milwaukee, Wis.
"dipropylene glycol," Aldrich
"polyvinylalcohol," Aldrich
"polyvinylpyrrolidone K-90," GAF® Chem. Co., Wayne, N.J.
"trehalose," Sigma
"L-sorbose," Sigma
"lactose," Sigma
"D-glucose," Sigma
"raffinose," Sigma
"melezitose," Sigma
"D-fructose," Sigma
"L-arabinose," Sigma
"starch,"
"sorbitol," Pfizer
"cyclodextrin," American Maize-Product Co., Hammond, Ind.
"D-ribose," Sigma
"pectin," Sigma
"gum guar," Sigma
"gum tragacantha," Sigma
"gum arabic," Sigma
"kappa carrageenan," Sigma
"maltose," Sigma
"polyethylene glycol (Carbowax® PEG-1450)," Union Carbide "ATCC 9372" *Bacillus subtilis* was grown for 16 hours at 37° C. in tryptic soy broth. This culture was used to inoculate the surface of agar plates consisting of 8 g/l nutrient broth, 0.011 g/l manganese sulfate, and 20 g/l agar at pH 7.2. The plates were incubated at 37° C. for 6 days and the spores were scraped from the plates and suspended in sterile distilled water. The spores were separated from vegetative debris by centrifuging the suspension at 7000 rpm and 4° C. for 20 minutes. The supernatant was poured off and the spores were resuspended in sterile distilled water. This cleaning procedure was repeated several times.

The *Bacillus subtilis* spores were coated and dried on 6.35×28.58 mm (¼×⅛ inch) strips of filter paper as described in Example 1 at a population of 1×10⁶ spores per strip. The spore strips of *Bacillus subtilis* were coated with a solution of one of the immobilizers listed above at percent concentrations (w/v) specified in Tables 17, 18, and 19, as described in Example 1, and allowed to dry.

Devices were assembled using the immobilized spore strips, as shown in FIGS. 1 and 2 and as described in Example 3.

Three unit batches of the devices described above and the control made in accordance with Example 1, both placed in metal instrument trays, and conventional biological indicators ("Attest™ Rapid Readout 1264 Biological Indicator") in "Attest™ 1278 test packs" (Lot #215, June 1992), commercially available from 3M, St. Paul, Minn., were preconditioned at 54° C. and 60% relative humidity for 30 minutes and then exposed for 15, 18, 21, 24, 27, and 30 minute intervals at 54° C. and 60% relative humidity, to 600 mg/L of ethylene oxide in a "Joslyn EO Bier Vessel," ethylene oxide sterilizer, commercially available from Joslyn Valve, Macedon, N.Y.

After exposure, the inner ampoules of the devices of the invention were aseptically removed and 0.67 ml of a solution of 17 g/L bacteriological peptone, 0.17 g/L L-alanine, and 0.03 g/L triphenyltetrazolium chloride was added to the outer vial of each unit. The conventional biological indicators were removed from the test packs and their inner ampoules crushed. All units were incubated at 37° C. Spore growth, as indicated by a color change produced by the pH indicator, was visually determined at 24, 48, and 168 hours of incubation.

The results are reported in Table 14.

TABLE 14

| Ethylene Oxide Exposure - Number Positive/3 Units Tested | | | | | |
|---|---|---|---|---|---|
| Sample | Immobilizer (W/V) | Exposure Time (min) | Spore outgrowth at | | |
| | | | 24 hr | 48 hr | 168 hr |
| Attest ™ 1264 | — | 15 | 3 | 3 | 3 |
| BI in Attest ™ 1278 Test Pack | | 18 | 3 | 3 | 3 |
| | | 21 | 2 | 2 | 2 |
| | | 24 | 0 | 0 | 0 |
| | | 27 | 0 | 0 | 0 |
| | | 30 | 0 | 0 | 0 |
| BI of Invention | Maltose (50%) | 15 | 3 | 3 | 3 |
| | | 18 | 3 | 3 | 3 |
| | | 21 | 3 | 3 | 3 |
| | | 24 | 3 | 3 | 3 |
| | | 27 | 0 | 0 | 0 |
| | | 30 | 0 | 0 | 0 |
| BI of Invention | D-Mannitol (30%) | 15 | 3 | 3 | 3 |
| | | 18 | 3 | 3 | 3 |
| | | 21 | 3 | 3 | 3 |
| | | 24 | 3 | 3 | 3 |
| | | 27 | 3 | 3 | 3 |
| | | 30 | 3 | 3 | 3 |
| BI of Invention | Myo-inositol (10%) | 15 | 3 | 3 | 3 |
| | | 18 | 3 | 3 | 3 |
| | | 21 | 3 | 3 | 3 |
| | | 24 | 3 | 3 | 3 |
| | | 27 | 3 | 3 | 3 |
| | | 30 | 3 | 3 | 3 |
| BI of Invention | Dulcitol (30%) | 15 | 3 | 3 | 3 |
| | | 18 | 3 | 3 | 3 |
| | | 21 | 3 | 3 | 3 |
| | | 24 | 3 | 3 | 3 |
| | | 27 | 3 | 3 | 3 |
| | | 30 | 3 | 3 | 3 |
| BI of Invention | D(+)-Cellobiose (10%) | 15 | 3 | 3 | 3 |
| | | 18 | 3 | 3 | 3 |
| | | 21 | 3 | 3 | 3 |
| | | 24 | 3 | 3 | 3 |
| | | 27 | 3 | 3 | 3 |
| | | 30 | 3 | 3 | 3 |
| BI of Invention | Glycerol | 15 | 3 | 3 | 3 |

TABLE 14-continued

Ethylene Oxide Exposure - Number Positive/3 Units Tested

| Sample | Immobilizer (W/V) | Exposure Time (min) | Spore outgrowth at | | |
|---|---|---|---|---|---|
| | | | 24 hr | 48 hr | 168 hr |
| | (40%) | 18 | 3 | 3 | 3 |
| | | 21 | 3 | 3 | 3 |
| | | 24 | 3 | 3 | 3 |
| | | 27 | 3 | 3 | 3 |
| | | 30 | 0 | 0 | 0 |
| BI of Invention | D-Glucose (50%) | 15 | 3 | 3 | 3 |
| | | 18 | 3 | 3 | 3 |
| | | 21 | 3 | 3 | 3 |
| | | 24 | 3 | 3 | 3 |
| | | 27 | 1 | 2 | 2 |
| | | 30 | 0 | 0 | 0 |
| BI of Invention | Starch (30%) | 15 | 3 | 3 | 3 |
| | | 18 | 3 | 3 | 3 |
| | | 21 | 3 | 3 | 3 |
| | | 24 | 1 | 2 | 2 |
| | | 27 | 0 | 0 | 0 |
| | | 30 | 0 | 0 | 0 |
| BI of Invention | Dipropylene glycol (50%) | 15 | 3 | 3 | 3 |
| | | 18 | 3 | 3 | 3 |
| | | 21 | 3 | 3 | 3 |
| | | 24 | 1 | 1 | 1 |
| | | 27 | 1 | 1 | 1 |
| | | 30 | 0 | 0 | 0 |
| BI of Invention | Sucrose (50%) | 15 | 3 | 3 | 3 |
| | | 18 | 3 | 3 | 3 |
| | | 21 | 3 | 3 | 3 |
| | | 24 | 3 | 3 | 3 |
| | | 27 | 3 | 3 | 3 |
| | | 30 | 0 | 2 | 2 |
| BI of Invention | D-Ribose (60%) | 15 | 3 | 3 | 3 |
| | | 18 | 3 | 3 | 3 |
| | | 21 | 3 | 3 | 3 |
| | | 24 | 2 | 2 | 2 |
| | | 27 | 0 | 0 | 0 |
| | | 30 | 0 | 0 | 0 |
| BI of Invention | D-arabinotol (10%) | 15 | 3 | 3 | 3 |
| | | 18 | 3 | 3 | 3 |
| | | 21 | 3 | 3 | 3 |
| | | 24 | 3 | 3 | 3 |
| | | 27 | 3 | 3 | 3 |
| | | 30 | 3 | 3 | 3 |
| BI of Invention | Trehalose (50%) | 15 | 3 | 3 | 3 |
| | | 18 | 3 | 3 | 3 |
| | | 21 | 3 | 3 | 3 |
| | | 24 | 3 | 3 | 3 |
| | | 27 | 3 | 3 | 3 |
| | | 30 | 0 | 1 | 1 |
| BI of Invention | Lactose (40%) | 15 | 3 | 3 | 3 |
| | | 18 | 3 | 3 | 3 |
| | | 21 | 3 | 3 | 3 |
| | | 24 | 3 | 3 | 3 |
| | | 27 | 3 | 3 | 3 |
| | | 30 | 3 | 3 | 3 |
| BI of Invention | Raffinose (30%) | 15 | 3 | 3 | 3 |
| | | 18 | 3 | 3 | 3 |
| | | 21 | 3 | 3 | 3 |
| | | 24 | 3 | 3 | 3 |
| | | 27 | 3 | 3 | 3 |
| | | 30 | 3 | 3 | 3 |
| BI of Invention | Melezitose (20%) | 15 | 3 | 3 | 3 |
| | | 18 | 3 | 3 | 3 |
| | | 21 | 3 | 3 | 3 |
| | | 24 | 3 | 3 | 3 |
| | | 27 | 3 | 3 | 3 |
| | | 30 | 3 | 3 | 3 |
| BI of Invention | Adonitol (50%) | 15 | 3 | 3 | 3 |
| | | 18 | 3 | 3 | 3 |
| | | 21 | 0 | 3 | 3 |
| | | 24 | 1 | 3 | 3 |
| | | 27 | 3 | 3 | 3 |
| | | 30 | 0 | 1 | 1 |
| BI of Invention | Xylitol | 15 | 3 | 3 | 3 |
| | (20%) | 18 | 3 | 3 | 3 |
| | | 21 | 2 | 3 | 3 |
| | | 24 | 0 | 3 | 3 |
| | | 27 | 0 | 2 | 2 |
| | | 30 | 0 | 0 | 0 |
| BI of Invention | D-fructose (30%) | 15 | 3 | 3 | 3 |
| | | 18 | 3 | 3 | 3 |
| | | 21 | 2 | 3 | 3 |
| | | 24 | 0 | 1 | 1 |
| | | 27 | 0 | 0 | 0 |
| | | 30 | 0 | 0 | 0 |
| BI of Invention | D-Arabinose (20%) | 15 | 3 | 3 | 3 |
| | | 18 | 3 | 3 | 3 |
| | | 21 | 3 | 3 | 3 |
| | | 24 | 3 | 3 | 3 |
| | | 27 | 1 | 3 | 3 |
| | | 30 | 2 | 2 | 2 |
| BI of Invention | Myo-Erythritol (20%) | 15 | 3 | 3 | 3 |
| | | 18 | 3 | 3 | 3 |
| | | 21 | 3 | 3 | 3 |
| | | 24 | 3 | 3 | 3 |
| | | 27 | 3 | 3 | 3 |
| | | 30 | 3 | 3 | 3 |
| BI of Invention | L-Sorbose (20%) | 15 | 3 | 3 | 3 |
| | | 18 | 3 | 3 | 3 |
| | | 21 | 3 | 3 | 3 |
| | | 24 | 3 | 3 | 3 |
| | | 27 | 3 | 3 | 3 |
| | | 30 | 3 | 3 | 3 |
| BI of Invention | Polyvinyl/pyrolidone (1%) | 15 | 3 | 3 | 3 |
| | | 18 | 3 | 3 | 3 |
| | | 21 | 3 | 3 | 3 |
| | | 24 | 0 | 0 | 0 |
| | | 27 | 0 | 0 | 0 |
| | | 30 | 0 | 0 | 0 |
| BI of Invention | Pectin (0.75%) | 15 | 3 | 3 | 3 |
| | | 18 | 0 | 3 | 3 |
| | | 21 | 0 | 3 | 3 |
| | | 24 | 0 | 2 | 2 |
| | | 27 | 0 | 0 | 0 |
| | | 30 | 0 | 0 | 0 |
| BI of Invention | Polyvinyl Alcohol (0.75%) | 15 | 3 | 3 | 3 |
| | | 18 | 3 | 3 | 3 |
| | | 21 | 3 | 3 | 3 |
| | | 24 | 1 | 3 | 3 |
| | | 27 | 0 | 0 | 0 |
| | | 30 | 0 | 0 | 0 |
| BI of Invention | Sorbitol (30%) | 15 | 3 | 3 | 3 |
| | | 18 | 3 | 3 | 3 |
| | | 21 | 3 | 3 | 3 |
| | | 24 | 1 | 3 | 3 |
| | | 27 | 2 | 3 | 3 |
| | | 30 | 1 | 1 | 1 |
| BI of Invention | Polyol-P (40%) | 15 | 3 | 3 | 3 |
| | | 18 | 3 | 3 | 3 |
| | | 21 | 3 | 3 | 3 |
| | | 24 | 1 | 3 | 3 |
| | | 27 | 0 | 0 | 0 |
| | | 30 | 0 | 0 | 0 |
| BI of Invention | PEG-1450 (30%) | 15 | 3 | 3 | 3 |
| | | 18 | 3 | 3 | 3 |
| | | 21 | 3 | 3 | 3 |
| | | 24 | 2 | 3 | 3 |
| | | 27 | 0 | 0 | 0 |
| | | 30 | 0 | 0 | 0 |
| BI of Invention | Gum guar (0.50%) | 15 | 3 | 3 | 3 |
| | | 18 | 3 | 3 | 3 |
| | | 21 | 3 | 3 | 3 |
| | | 24 | 2 | 3 | 3 |
| | | 27 | 0 | 0 | 0 |
| BI of Invention | Gum arabic | 15 | 3 | 3 | 3 |

TABLE 14-continued

Ethylene Oxide Exposure - Number Positive/3 Units Tested

| Sample | Immobilizer (W/V) | Exposure Time (min) | Spore outgrowth at 24 hr | 48 hr | 168 hr |
|---|---|---|---|---|---|
| | (0.75%) | 18 | 3 | 3 | 3 |
| | | 21 | 0 | 3 | 3 |
| | | 24 | 0 | 0 | 0 |
| | | 27 | 0 | 0 | 0 |
| | | 30 | 0 | 0 | 0 |
| BI of Invention | Gum tragacantha (1%) | 15 | 3 | 3 | 3 |
| | | 18 | 3 | 3 | 3 |
| | | 21 | 2 | 3 | 3 |
| | | 24 | 1 | 3 | 3 |
| | | 27 | 1 | 1 | 1 |
| | | 30 | 0 | 0 | 0 |
| BI of Invention | Kappa carrageenan (0.75%) | 15 | 3 | 3 | 3 |
| | | 18 | 3 | 3 | 3 |
| | | 21 | 2 | 3 | 3 |
| | | 24 | 0 | 1 | 1 |
| | | 27 | 0 | 0 | 0 |
| | | 30 | 0 | 0 | 0 |
| BI of Invention | Cyclodextrin (1.0%) | 15 | 3 | 3 | 3 |
| | | 18 | 3 | 3 | 3 |
| | | 21 | 3 | 3 | 3 |
| | | 24 | 3 | 3 | 3 |
| | | 27 | 3 | 3 | 3 |
| | | 30 | 0 | 0 | 0 |
| Control | — | 15 | 3 | 3 | 3 |
| | | 18 | 3 | 3 | 3 |
| | | 21 | 0 | 0 | 0 |
| | | 24 | 0 | 0 | 0 |
| | | 27 | 0 | 0 | 0 |
| | | 30 | 0 | 0 | 0 |

The data demonstrates that immobilized *Bacillus subtilis* spores used without conventional test packs provide ethylene oxide sterilization indicators with survival/kill time points as good as or better than conventional ethylene oxide biological indicators in conventional test packs. However, spore survival after 30 minute exposures indicates a need to decrease the immobilizer concentration in order for the indicator of the invention to simulate conventional biological indicator test packs.

Example 11

This example illustrates the use of the compounds listed in Table 15 (polyols and related compounds need broad description for immobilizing compounds useful with ethylene oxide) to immobilize *Bacillus subtilis* spores and their exoenzyme beta-glucosidase.

"ATCC 9372" *Bacillus subtilis* spores were grown as described in Example 10. The *Bacillus subtilis* spores were coated, dried, and immobilized as described in Example 10, except at a population of $1 \times 10^7$ spores per strip.

Devices were assembled using the immobilized spore strips, as shown in FIGS. 3 and 4, and as described in Example 1.

Three unit batches of these devices were placed in metal instrument trays along with the unit batches of conventional biological indicators. "Attest™ Ethylene Oxide Biological Indicator 1264" in "1278 Attest™ Test Packs," (Lot #215, June 1992) commercially available from 3M, St. Paul, Minn. The invention and the conventional biological indicators in test packs were preconditioned at 54° C. and 60% relative humidity for 30 minutes. The devices were then exposed for 20, 30, 60, and 120 minutes at 54° C. and 60% relative humidity, to 600 mg/l of ethylene oxide in a "Joslyn EO Bier Vessel," commercially available from Joslyn Valve, Macedon, N.Y.

After exposure, the inner ampoules of the devices of the invention were removed aseptically, and 0.67 ml of a solution of 17 g/l bacteriological peptone, 0.17 g/l L-alanine, 0.03 g/l triphenyltetrazolium chloride, and 0.1 g/l of 4-methylumbelliferyl-beta-D-glucoside, commercially available from Sigma Chemical Co., St. Louis, Mo., was added to each unit. The conventional biological indicators were removed from the test packs and their inner ampoules crushed. All units were incubated at 37° C. An "Attest™ 190 Auto-Reader", commercially available from 3M, was used to fluorometrically read beta-glucosidase activity by measuring 4-methylumbelliferyl fluorescence after 8 hours of incubation. Spore growth, as indicated by a color change produced by the pH indicator, was visually determined at 24, 48, and 168 hours of incubation.

The results are reported in Table 15.

TABLE 15

Ethylene Oxide Exposure - Number Positive/3 Units Tested

| Sample | Immobilizer (W/V) | Exposure Time (min) | Fluorescence 8 hr | Spore Outgrowth at 24 hr | 48 hr | 168 hr |
|---|---|---|---|---|---|---|
| 1264 Attest ™ BI in 1278 Attest ™ Test Pack | — | 20 | — | 3 | 3 | 3 |
| | | 30 | | 0 | 0 | 0 |
| | | 60 | | 0 | 0 | 0 |
| | | 120 | | 0 | 0 | 0 |
| BI of Invention | Mannitol (30%) | 20 | 3 | 3 | 3 | 3 |
| | | 30 | 3 | 3 | 3 | 3 |
| | | 60 | 3 | 3 | 3 | 3 |
| | | 120 | 3 | 3 | 3 | 3 |
| BI of Invention | Sucrose (50%) | 20 | 3 | 3 | 3 | 3. |
| | | 30 | 3 | 3 | 3 | 3 |
| | | 60 | 0 | 0 | 0 | 0 |
| | | 120 | 0 | 0 | 0 | 0 |
| BI of Invention | Cellobios (10%) | 20 | 3 | 3 | 3 | 3 |
| | | 30 | 3 | 3 | 3 | 3 |
| | | 60 | 0 | 0 | 0 | 0 |
| | | 120 | 0 | 0 | 0 | 0 |
| BI of Invention | Erythitol | 20 | 3 | 3 | 3 | 3 |

TABLE 15-continued

Ethylene Oxide Exposure - Number Positive/3 Units Tested

| Sample | Immobilizer (W/V) | Exposure Time (min) | Fluorescence 8 hr | Spore Outgrowth at 24 hr | 48 hr | 168 hr |
|---|---|---|---|---|---|---|
| | (20%) | 30 | 3 | 3 | 3 | 3 |
| | | 60 | 0 | 0 | 0 | 0 |
| | | 120 | 0 | 0 | 0 | 0 |
| BI of Invention | Cyclodextrin (6%) | 20 | 3 | 3 | 3 | 3 |
| | | 30 | 3 | 3 | 3 | 3 |
| | | 60 | 3 | 3 | 3 | 3 |
| | | 120 | 3 | 3 | 3 | 3 |
| BI of Invention | Arabinose (50%) | 20 | 3 | 3 | 3 | 3 |
| | | 30 | 3 | 3 | 3 | 3 |
| | | 60 | 3 | 3 | 3 | 3 |
| | | 120 | 3 | 3 | 3 | 3 |
| BI of Invention | Sorbose (30%) | 20 | 3 | 3 | 3 | 3 |
| | | 30 | 3 | 3 | 3 | 3 |
| | | 60 | 3 | 3 | 3 | 3 |
| | | 120 | 3 | 3 | 3 | 3 |
| BI of Invention | Xylitol (50%) | 20 | 3 | 3 | 3 | 3 |
| | | 30 | 3 | 3 | 3 | 3 |
| | | 60 | 3 | 3 | 3 | 3 |
| | | 120 | 3 | 3 | 3 | 3 |
| BI of Invention | Glycerin (40%) | 20 | 3 | 3 | 3 | 3 |
| | | 30 | 3 | 3 | 3 | 3 |
| | | 60 | 3 | 3 | 3 | 3 |
| | | 120 | 3 | 3 | 3 | 3 |
| BI of Invention | Adontiol (50%) | 20 | 3 | 3 | 3 | 3 |
| | | 30 | 3 | 3 | 3 | 3 |
| | | 60 | 0 | 0 | 0 | 0 |
| | | 120 | 0 | 0 | 0 | 0 |

The data demonstrates that immobilized *Bacillus subtilis* spores used without conventional test packs provide ethylene oxide sterilization indicators with survival/kill time points as good as or better than conventional ethylene oxide biological indicators in conventional test packs. However, spore survival after 30 minute exposures indicates a need to decrease the immobilizer concentration in order for the indicator of the invention to simulate conventional biological indicator test packs.

Example 12

This example illustrates that biological indicators of this invention, which include alpha-glucosidase immobilized by adsorption onto insoluble support materials, provide sterilization efficacy results comparable to conventional biological indicators in AAMI sixteen towel test packs at 250° F. (121° C.) gravity exposures.

Preparation of Enzyme

Purified "alpha-glucosidase" (Lot #001) from *Bacillus stearothermophilus* was obtained from Unitika LTD., Kyoto, Japan. Lyophilized alpha-glucosidase (10,000 units) with specific activity of 100 units/mg protein, was suspended in 1 ml of sterile distilled water. This suspension was dialyzed for 24 hours against 1 liter of sterile distilled water using a "Spectra/Por® Molecularporous Membrane", commercially available from Spectrum Medical Industries Inc., Los Angeles, Calif., at a molecular weight cutoff of 3500 daltons. The dialyzed enzyme suspension was stored at 4° C. until needed. Dilutions of dialyzed alpha-glucosidase were made in sterile distilled water to give a 50 ml suspension at an enzyme concentration of 200 units/ml.

Immobilization of Enzyme

Immobilization of the enzyme by adsorption onto the support materials "DEAE-Sephadex® A-50", "CM-Sephadex® C-50", both commercially available from Pharmacia Fine Chemicals, Piscataway, N.J.; "Silica Gel 60 Angstroms" commercially available from American Scientific Products, McGraw Park, Ill.; hydroxylapatite and calcium carbonate, both commercially available from EM Science, Cherry Hill, N.J., was accomplished by the following method.

The five support materials were equilibrated by suspension in appropriate buffer solutions as follows. DEAE-Sephadex, 0.5 g; silica gel, 1 g; hydroxylapatite, 1 g; and calcium carbonate, 1 g, were suspended into separate 100 ml solutions of 0.01M potassium phosphate buffer, pH 7.3, and allowed to equilibrate for 2 days at ambient conditions. CM-Sephadex, 0.5 g, was suspended into 100 ml of 0.01M sodium acetate buffer, pH 4.6, and allowed to equilibrate for 2 days. The equilibrated support materials were then centrifuged at 7000 rpm, at 4° C., for 30 minutes, and the supernatant was discarded. The pellets of support materials were then resuspended by adding 10 ml of alpha-glucosidase solution, 200 units/ml, and mixing gently for 1 hour under ambient conditions using an orbital shaker.

The enzyme/support complex was pelleted by centrifugation at 7000 rpm, at 4° C., for 15 minutes. The supernatant was decanted and saved. The enzyme/support complex was allowed to dry under ambient conditions for 4 days. The dried enzyme/support complex was stored at 4° C. until needed.

Measurement of the amount of alpha-glucosidase immobilized onto the five support materials was done by determining the amount of enzyme activity in units remaining in supernatant collected after immobilization of the alpha-glucosidase onto the support material as follows.

Nine hundred microliters of 20 mM p-nitrophenyl-alpha-D-glucopyranoside commercially available from Sigma Chemical Co., St. Louis, Mo., in sterile distilled water was mixed in a test tube with 100 microliters of a 1:100 dilution in distilled water of the supernatant. After 15 minutes at 30°

C., 1000 microliters of 0.2M sodium carbonate was added to the test tube to terminate the enzyme-substrate reaction. The increase in absorbance at 400 nm due to the generation of substrate product, p-nitrophenol, was determined against controls from which the enzyme was omitted. A mole extinction coefficient of 18.1 cm$^2$ per micromole was used to calculate the amount of substrate product contained in the supernatant. One unit of enzyme activity is defined as the amount of alpha-glucosidase that forms 1 micromole of p-nitrophenol per minute at 30° C. The units of enzyme contained in the supernatant were subtracted from 2,000 units to yield the units of enzyme contained in the dried enzyme/support complex. The units of enzyme in the dried enzyme/support products is reported in Table 16.

Assembly of Devices

Devices were constructed as illustrated in FIGS. 3 and 4, and described in Example 1, except that 0.1 g of the dried enzyme/support product was placed in the outer container 40 prior to placing the barrier 47 within the outer container.

Three unit batches of the devices of the invention, consisting of immobilized alpha-glucosidase, were placed in metal instrument trays. Three "Attest™ Biological indicators 1262/1262P" and three "Attest™ Rapid Readout Biological Indicators 1291" commercially available from 3M, St. Paul, Minn., were placed within AAMI steam test packs between the 8th and 9th towels from the bottom of the stack. The test packs were secured with autoclave tape.

The devices of the invention and the conventional AAMI biological test packs were exposed for 16, 18, and 20 minute intervals at 250° F. (132°C.) gravity in an "Amsco Eagle™ Model 3000," steam sterilizer. Following exposure, the conventional biological indicators were removed from the AAMI sixteen towel test packs. The inner ampoules of the devices of the invention and the conventional biological indicators were crushed and the units were incubated at 60° C. An "Attest™ 190 Auto-Reader" was used to read alpha-glucosidase activity by measuring 4-methylumbelliferyl fluorescence after 4 and 8 hours of incubation. The results are reported in Table 17.

TABLE 16

Enzyme Immobilized by Adsorption on Support

| Support | Alpha-glucosidase in supernatant (units) | Immobilized Alpha-glucosidase on support (units) |
|---|---|---|
| DEAE-Sephadex ® | 50 | 150 |
| CM-Sephadex ® | 25 | 175 |
| Silica Gel | 100 | 100 |
| Hydroxylapatite | 110 | 90 |
| Calcium Carbonate | 100 | 100 |

TABLE 17

250° F. Gravity Exposure - Number Positive/3 units Testes

| Sample | Exposure Time (min) | Fluorescence 4 hr | Fluorescence 8 hr | Spore Outgrowth at 24 hr | 48 hr | 168 hr |
|---|---|---|---|---|---|---|
| Attest ™ 1261/ | 16 | — | — | 2 | 2 | 2 |
| 1262P BI in AAMI | 18 | | | 0 | 0 | 0 |
| Test Pack | 20 | | | 0 | 0 | 0 |
| Attest ™ 1291 BI in | 16 | 2 | 2 | 2 | 2 | 2 |
| AAMI Test Pack | 18 | 0 | 0 | 0 | 0 | 0 |
| | 20 | 0 | 0 | 0 | 0 | 0 |

TABLE 17-continued

250° F. Gravity Exposure - Number Positive/3 units Testes

| Sample | Exposure Time (min) | Fluorescence 4 hr | Fluorescence 8 hr | Spore Outgrowth at 24 hr | 48 hr | 168 hr |
|---|---|---|---|---|---|---|
| DEAE-Sephadex ® | 16 | 3 | 3 | — | — | — |
| immobilized enzyme | 18 | 3 | 3 | | | |
| (150 units) | 20 | 0 | 0 | | | |
| CM-Sephadex ® | 16 | 3 | 3 | — | — | — |
| immobilized enzyme | 18 | 0 | 0 | | | |
| (175 units) | 20 | 0 | 0 | | | |
| Silica Gel immobilized | 16 | 3 | 3 | — | — | — |
| enzyme (100 units) | 18 | 1 | 1 | | | |
| | 20 | 0 | 0 | | | |
| Hydroxylapatite | 16 | 2 | 2 | — | — | — |
| immobilized enzyme | 18 | 0 | 0 | | | |
| (90 units) | 20 | 0 | 0 | | | |
| Calcium carbonate | 16 | 3 | 3 | — | — | — |
| immobilized enzyme | 18 | 0 | 0 | | | |
| (100 units) | 20 | 0 | 0 | | | |

The symbol (—) indicates that these readings were not taken.

The data presented above demonstrates that the biological indicators of the invention, utilizing alpha-glucosidase immobilized by adsorption onto various water-insoluble support carriers can provide survival/kill results comparable with conventional biological indicators in AAMI test packs.

Example 13

This example illustrates the use of chemical immobilizer, D-Sorbitol, to enhance the survival/kill performance of the spore bound enzyme and spores when used with and without conventional test packs (as shown in FIGS. 5 & 6) in a European Sterilization Equipment Company prevacuum steam sterilization cycle (121° C).

Bacillus stearothermophilus spores were grown, coated on filter paper and immobilized with "D-Sorbitol," as described in Example 1. Biological indicators of this invention were constructed as illustrated in FIGS. 3 and 4 and as described in Example 1.

Assembly of Test Packs

Test packs were constructed as shown in FIGS. 5 and 6. The test pack 100 comprised a box 102 having overall dimensions of 134 mm (5.36 in) by 140 mm (5.60 in) by 28 mm (1.12 in). The box was made of bleached sulfate paper unvarnished.

The box contained an open container 108 also made of bleached sulfate paper which was coated on its exterior surfaces with a steam impermeable thermoplastic coating 110 of polypropylene laminate. Container 108 was dimensioned to be only slightly smaller than the box 102.

Two stacks of sheets, 112 and 114, of semi-porous material separated by a stack of sheets 116 also of semi-porous material were contained in container 108. Each stack of semi-porous material was formed of filter paper having an approximate basis weight of 214 pounds (7 kg) per 3,000 square feet (280m) and an approximate thickness of 1 mm per sheet. Stacks 112 and 114 included 36 sheets of filter paper.

The semi-porous stack 116 was composed of 16 sheets of filter paper with a 13 mm by 49 mm area 118 cut from the center of each sheet in order to receive biological indicator 11 of this invention. The height of this central core, when assembled and dry, was approximately 10 mm.

The test pack was opened by opening the box flap 122, the top semi-porous sheets were removed and a conventional biological indicator or a biological indicator of this invention surrounded by a coiled metal spring 120, preferably made of stainless steel, was placed within the cavity in the center portion of the stack. The top sheets were then replaced and the box closed.

Comparative Test

The devices of the invention, used alone and in the above-described test packs, and controls consisting of conventional "Attest™ 1262 Biological Indicators" and "Attest™ 1291 Rapid Readout Biological Indicators" in the above-described test packs were placed in metal trays and exposed for 6, 6.5, 7, and 15 minute intervals to a 121° C. (250° F.) prevacuum sterilization cycle, 3 negative pulses, in a gravity displacement and vacuum assisted sterilizer, commercially available as a "Getinge™ PACs 2000 High Vacuum Sterilizer", from Getinge™ International, Inc., Lakewood, N.J. The settings on the sterilizer were as indicated in Table 18. The cycle is a European Sterilization Equipment Company prevacuum cycle. Following exposure, the biological indicators were evaluated as described in Example 1. The results are reported in Table 19.

TABLE 18

| Getinge ™ PACs 200 High Vacuum Sterilizer | | |
|---|---|---|
| Prevacuum Pulses | 3.0 | Pulses |
| Prevacuum Depth | 0.066 | Bar |
| Vacuum Hold Time | 00:00:10 | Minutes |
| Steam Charge Level | 0.900 | Bar |
| Evacuation Ramp | 5.0 | Bar/Minute |
| Steam Pressure | 5.0 | Bar/Minute |
| Sterilize | 100.0 | Bar/Minute |
| Exposure Temperature | 121.0 | Celsius |
| Postvacuum Depth | 0.0060 | Bar |

Example 14

Example 14 illustrates the use of chemical immobilizer D-sorbitol to enhance the survival/kill performance of the spore bound enzyme and spore when used with and without conventional test packs (as shown in FIGS. 5 & 6) in a European Sterilization Equipment Company prevacuum steam sterilization cycle (134° C. (272° F.)).

*Bacillus stearothermophilus* commercially available as "ATCC 7953" from American Type Culture Collection, Rockville, Md., was grown as described in Example 1. The *Bacillus stearothermophilus* spores were coated on filter paper, dried, and immobilized as described in Example 1. Biological indicator devices were constructed utilizing the immobilized spore strip as described in Example 1 and illustrated in FIGS. 3 and 4.

Three unit batches of the devices containing immobilized *Bacillus stearothermophilus* spores, used alone and in the test packs described in Example 13, and conventional "Attest™ 1262 Biological Indicators" and "Attest™ 1291 Rapid Readout Biological Indicators" in the conventional steam test packs described in Example 13, were placed in metal instrument trays. They were exposed for 0, 2, 4, 6, 8, 10, and 12 second intervals to a 134° C. (272° F.) prevacuum sterilization cycle, 3 negative pulses, 4 positive pulses in a gravity displacement and vacuum assisted sterilizer, commercially available as a "Getinge™ PACS 2000 High Vacuum Sterilizer", from Getinge International, Inc., Lakewood, N.J.

The settings for the sterilizer were as indicated in Table 20. The cycle is a European Sterilization Company prevacuum cycle. Following exposure, the biological indicators were evaluated as described in Example 1. The results are reported in Table 21.

TABLE 19

| 121° C. Exposure - Number Positive/3 Units Tested | | | | | | |
|---|---|---|---|---|---|---|
| | Immobilizer | Exposure | Fluorescence | Spore Outgrowth at | | |
| Sample | (w/v) | Time (min) | 4 hr | 24 hr | 48 hr | 168 hr |
| 1264 Attest ™ BI in Test | — | 6.0 | — | 5 | 5 | 5 |
| Pack | — | 6.5 | — | 0 | 2 | 2 |
| | — | 7.0 | — | 0 | 0 | 0 |
| | — | 15.0 | — | 0 | 0 | 0 |
| BI of Invention in Test | D-sorbitol | 6.0 | 5 | 5 | 5 | 5 |
| Pack | (10%) | 6.5 | 5 | 4 | 5 | 5 |
| | | 7.0 | 1 | 1 | 1 | 1 |
| | | 15.0 | 0 | 0 | 0 | 0 |
| BI of Invention Not | D-sorbitol | 6.0 | 5 | 5 | 5 | 5 |
| Contained in a Test Pack | (60%) | 6.5 | 5 | 4 | 5 | 5 |
| | | 7.0 | 5 | 5 | 5 | 5 |
| | | 15.0 | 0 | 0 | 0 | 0 |
| Attest ™ | — | 6.0 | — | 0 | 0 | 0 |
| 1291 BI in Test Pack | — | 6.5 | — | 0 | 0 | 0 |
| | — | 7.0 | — | 0 | 0 | 0 |
| | — | 15.0 | — | 0 | 0 | 0 |

The symbol (—) indicates that no immobilizer was used or that readings were not take.

The devices of this invention were designed to provide microbial challenge during exposure to steam sterilization cycles (including European sterilization cycles) which is equal to or greater than the microbial challenge provided by conventional test packs. The date reported in Table 19 demonstrates that the biological indicators of this invention (with and without test packs) achieve and outperform this requirement.

TABLE 20

| Getinge ™ PACs 2000 High Vacuum Sterilizer | | |
|---|---|---|
| Prevacuum Pulses | 3.00 | Pulses |
| Prevacuum Depth | 0.20 | Bar |
| Steam Charge Level | 0.90 | Bar |

TABLE 20-continued

Getinge ™ PACs 2000 High Vacuum Sterilizer

| Evacuation Ramp | 5.00 | Bar/Minute |
| Steam Pressure | 5.00 | Bar/Minute |
| Positive Pulses | 4.00 | Pulses |
| Steam Positive Exhaust | 1.20 | Bar |
| Steam Positve Charge | 2.60 | Bar |
| Sterilize | 135.0 | Bar/Minute |
| Exposure Temperature | 134.0 | Celsius |
| Postvacuum Depth | 0.66 | Bar |

Three unit batches of the devices containing immobilized *Bacillus stearothermophilus* spores, used alone and in the test packs described in Example 13, and conventional "Attest™ 1262 Biological indicators" and "Attest™ 1291 Rapid Readout Biological Indicators" in conventional steam test packs as described in Example 13, were places in metal instrument trays. They were exposed for 0, 2, 4, 6, 8, 10, and 12 second intervals to a 134° C. (272° F.) prevacuum sterilization cycle, 4 negative pulses in a gravity displacement and vacuum assisted sterilizer, commercially available as a "Getinge™ PACs 2000 High Vacuum Sterilizer", from Getinge™ International. The settings for the sterilizer were

TABLE 21

134° C. Prevacuum Exposure - Number Positive/3 Units Tested

| Sample | Immobilizer (w/v) | Exposure Time (min) | Fluorescence 4 hr | Spore Outgrowth at 24 hr | 48 hr | 168 hr |
|---|---|---|---|---|---|---|
| 1264 Attest ™ | — | 0 | — | 0 | 0 | 0 |
| 1262 BI in Test Pack | — | 2 | — | 0 | 0 | 0 |
|  | — | 4 | — | 0 | 0 | 0 |
|  | — | 6 | — | 0 | 0 | 0 |
|  | — | 8 | — | 0 | 0 | 0 |
|  | — | 10 | — | 0 | 0 | 0 |
|  | — | 12 | — | 0 | 0 | 0 |
| BI of Invention in Test Pack | D-sorbitol (50%) | 0 | 3 | 3 | 3 | 3 |
|  |  | 2 | 3 | 3 | 3 | 3 |
|  |  | 4 | 1 | 1 | 1 | 1 |
|  |  | 6 | 0 | 0 | 0 | 0 |
|  |  | 8 | 0 | 0 | 0 | 0 |
|  |  | 10 | 0 | 0 | 0 | 0 |
|  |  | 12 | 0 | 0 | 0 | 0 |
| BI of Invention Not Contained in a Test Pack | D-sorbitol (60%) | 0 | 3 | 3 | 3 | 3 |
|  |  | 2 | 3 | 2 | 3 | 3 |
|  |  | 4 | 1 | 1 | 1 | 1 |
|  |  | 6 | 2 | 1 | 2 | 2 |
|  |  | 8 | 1 | 1 | 1 | 1 |
|  |  | 10 | 1 | 1 | 1 | 1 |
|  |  | 12 | 0 | 0 | 0 | 0 |
| Attest ™ 1291 BI in Test Pack | — | 0 | 0 | 0 | 0 | 0 |
|  | — | 2 | 0 | 0 | 0 | 0 |
|  | — | 4 | 0 | 0 | 0 | 0 |
|  | — | 6 | 0 | 0 | 0 | 0 |
|  | — | 8 | 0 | 0 | 0 | 0 |
|  | — | 10 | 0 | 0 | 0 | 0 |
|  | — | 12 | 0 | 0 | 0 | 0 |

The symbol (—) indicates that no immobilizer was used or that readings were not taken.

The data in Table 21 above demonstrates that the biological indicators of the invention utilizing spores and spore bound enzyme immobilized with D-sorbitol (with and without test packs) provide a greater microbial challenge than do conventional biological indicators used in conventional steam sterilization test packs.

Example 15

This example illustrates the use of chemical D-sorbitol to enhance the survival/kill performance of the spore bound enzyme and spore when used with and without conventional test packs (as shown in FIGS. 5 & 6) in a German Industrial Norm prevacuum steam sterilization cycle (134° C. (272° F.)).

*Bacillus stearothermophilus* commercially available as "ATCC 7953" from American Type Culture Collection, Rockville, Md., were grown as described in Example 1. The *Bacillus Stearothermophilus* spores were coated on filter paper, dried, and immobilized as described in Example 1. Biological indicators were constructed utilizing the immobilized spore strip as described in Example 1 and illustrated in FIGS. 3 and 4.

as indicated in Table 22. The cycle is a German Industrial Norm prevacuum steam sterilization cycle.

Following exposure, the biological indicators were evaluated as described in Example 1. The results are reported in Table 23.

The 134° C. (272° F.) German Industrial Norm prevacuum cycle parameters are reported in Table 5. The results of the devices of the invention and control biological indicators are reported in Table 6. In the Tables of the Examples BI stands for "biological indicator".

TABLE 22

Getinge ™ PACs 2000 High Vacuum Sterilizer

| Prevacuum Pulses | 4.0 | Pulses |
| Prevacuum Depth | 0.060 | Bar |
| Vacuum Hold Time | 00:00:10 | Minutes |
| Steam Charge Level | 1.0 | Bar |
| Evacuation Ramp | 5.0 | Bar/Minute |
| Steam Pressure | 5.0 | Bar/Minute |

TABLE 22-continued

| Getinge ™ PACs 2000 High Vacuum Sterilizer | | |
|---|---|---|
| Sterilize | 100.0 | Bar/Minute |
| Exposure Temperature | 134.0 | Celsius |
| Postvacuum Depth | 0.060 | Bar |

TABLE 23

134° C. Prevacuum Exposure - Number Positive/3 Units Tested

| Sample | Immobilizer (w/v) | Exposure Time (min) | Fluorescence 4 hr | Spore Outgrowth at | | |
|---|---|---|---|---|---|---|
| | | | | 24 hr | 48 hr | 168 hr |
| Attest ™ 1262 BI in Test Pack | — | 0 | — | 0 | 0 | 0 |
| | — | 0.25 | — | 3 | 3 | 3 |
| | — | 1.0 | — | 3 | 3 | 3 |
| | — | 2.0 | — | 0 | 0 | 0 |
| | — | 3.0 | — | 0 | 0 | 0 |
| | — | 4.0 | — | 0 | 0 | 0 |
| BI of Invention in Test Pack | D-sorbitol (10%) | 0 | 3 | 3 | 3 | 3 |
| | | 0.25 | 3 | 3 | 3 | 3 |
| | | 1.0 | 3 | 3 | 3 | 3 |
| | | 2.0 | 0 | 0 | 0 | 0 |
| | | 3.0 | 0 | 0 | 0 | 0 |
| | | 4.0 | 0 | 0 | 0 | 0 |
| BI of Invention Not Contained in a Test Pack | D-sorbitol (60%) | 0 | 3 | 3 | 3 | 3 |
| | | 0.25 | 3 | 3 | 3 | 3 |
| | | 1.0 | 1 | 1 | 3 | 3 |
| | | 2.0 | 0 | 0 | 0 | 0 |
| | | 3.0 | 0 | 0 | 0 | 0 |
| | | 4.0 | 0 | 0 | 0 | 0 |
| Attest ™ 1291 BI in Test Pack | — | 0 | 3 | 3 | 3 | 3 |
| | — | 0.25 | 0 | 0 | 0 | 0 |
| | — | 1.0 | 0 | 0 | 0 | 0 |
| | — | 2.0 | 0 | 0 | 0 | 0 |
| | — | 3.0 | 0 | 0 | 0 | 0 |
| | — | 4.0 | 0 | 0 | 0 | 0 |

The symbol (—) indicates that no immobilizer was used or that readings were not taken.

The data in Table 23 above demonstrates that the biological indicators of the invention utilizing spores and spore bound enzyme immobilized with D-sorbitol, with and without test packs, provide survival/kill results comparable to conventional biological indicators used in conventional test packs.

What is claimed is:

1. An improved biological indicator comprising
   (a) an outer container having liquid impermeable walls, said container having at least one opening therein;
   (b) contained within said outer container a detectable amount of
      (1) a viable test microorganism useful to monitor a sterilization cycle or
      (2) another source of an active test enzyme useful to monitor the sterilization cycle,
   wherein the improvement comprises immobilizing the test microorganism or enzyme by means selected from the group consisting of
      (1) chemical reaction;
      (2) adsorption onto a water-insoluble support material selected from the group consisting of a dextran derivative, silica gel, hydroxylapetite, and calcium carbonate;
      (3) reaction with a water-insoluble support material capable of forming covalent or ionic bonds to the test microorganism or test enzyme;
      (4) entrapping the microorganism or enzyme within a crosslinked polymer gel matrix comprising non-ionic polymer-forming materials which are non-reactive with the microorganism or enzyme;
      (5) crosslinking with a crosslinking agent capable of forming intra- or inter-molecular crosslinks between the test microorganisms or test enzyme; and
      (6) microencapsulation;
   such immobilization being to an extent capable of allowing a detectable amount of said immobilized microorganism or enzyme to survive or remain active following an exposure to the sterilization cycle which is sublethal to the test microorganism when contained in a test pack commonly used to monitor sterilization, and incapable of allowing any detectable amount of immobilized microorganism or enzyme to survive or remain active following an exposure to the sterilization cycle which is lethal to the test microorganism when contained in the test pack commonly used to monitor sterilization.

2. The biological indicator of claim 1 wherein the test pack commonly used to monitor sterilization is an Association for the Advancement of Medical Instrumentation test pack.

3. The biological indicator of claim 1 wherein the sterilization cycle is an ethylene oxide cycle and the test microorganism or enzyme is immobilized with a chemical immobilizing agent selected from the group consisting of alditols, monosaccharides, polysaccharides, polylactams, and polymeric alcohols selected from the group consisting of polyvinyl alcohol, glycols and diols.

4. The biological indicator of claim 1 wherein said indicator further comprises:
   (c) a sealed, openable gas and liquid impermeable inner container, containing an aqueous nutrient medium capable, with incubation, of promoting growth of viable test microorganisms, said inner container being disposed in said outer container and said inner container, when opened, permitting said nutrient medium to contact said test microorganisms;

(d) a detector material contained in at least one of said inner or outer container and capable of undergoing a visible color change in response to growth of the test microorganisms.

5. The biological indicator of claim 1 comprising said source of active test enzyme and also comprising:

(c) within the outer container, a dectable amount of a said viable test microorganism capable of monitoring sterilization.

6. The biological indicator of claim 1 wherein the test microorganism or enzyme is immobilized by adsorption onto a water-insoluble support material.

7. The biological indicator of claim 6 wherein the water insoluble support material is capable of absorbing at least $1 \times 10^2$ test microorganisms in 0.1 unit of test enzyme.

8. The biological indicator of claim 1 wherein the test microorganism or enzyme is immobilized by a water-insoluble support material capable of forming covalent or ionic bonds to the test microorganism or test enzyme.

9. The biological indicator of claim 8 wherein the water-insoluble support material is capable of forming covalent or ionic bonds to at least $1 \times 10^2$ test microorganisms or 0.1 unit of test enzyme.

10. The biological indicator of claim 1 wherein the test microorganism or test enzyme is immobilized by entrapping the microorganism or enzyme within a crosslinked polymer gel matrix comprising non-ionic polymer-forming materials which are non-reactive with the microorganism or enzyme.

11. The biological indicator of claim 10 wherein at least $1 \times 10^2$ test microorganisms or 0.1 unit of test enzyme is entrapped within the crosslinked polymer gel matrix.

12. The biological indicator of claim 1 wherein the test microorganism or enzyme is immobilized by a crosslinking agent capable of forming intra- or inter-molecular cross links between the test microorganisms or test enzyme.

13. The biological indicator of claim 12 wherein the crosslinking agent is capable of forming intra- or intermolecular cross links between at least $1 \times 10^2$ test microorganisms or 0.1 unit of test enzyme.

14. The biological indicator of claim 1 wherein the test microorganism or test enzyme are immobilized by microencapsulation.

15. The biological indicator of claim 14 wherein at least $1 \times 10^2$ test microorganisms or 0.1 unit of test enzyme are immobilized.

16. The biological indicator of claim 1 wherein the test microorganism is selected from Bacillus, Clostridium, Candida or Neurospura species of microorganism.

17. The biological indicator of claim 16 wherein the test microorganism is *Bacillus stearothermophilus* or *Bacillus subtilis*.

18. The biological indicator of claim 1, wherein said source of active test enzyme is isolated enzyme derived from a microorganism, animal or plant.

19. The biological indicator of claim 18 wherein said test enzyme is selected from the group consisting of beta-D-glucosidase, alpha-D-glucosidase, alkaline phosphatase, acid phosphatase, butyrate esterase, caprylate esterase lipase, myristate lipase, leucine aminopeptidase, valine aminopeptidase, chymotrypsin, phosphohydrolase, alpha-D-galactosidase, beta-D-galactosidase, alpha-L-arabinofuranosidase, beta-D-glucuronidase, N-acetyl-b-glucosaminidase, beta-D-cellobiosidase, alanine aminopeptidase, proline aminopeptidase, tyrosine aminopeptidase, leucine aminopeptidase, phenylalanine aminopeptidase and a fatty acid esterase derived from spore-forming microorganisms.

20. The biological indicator of claim 1 wherein the sterilization cycle is a steam cycle and the test microorganism or enzyme is immobilized with a chemical immobilizing agent selected from the group consisting of alditols, disaccharides, trisaccharides, and polymeric alcohols selected from the group consisting of polyvinyl alcohol, glycols and diols.

21. The biological indicator of claim 20 wherein the immobilizing agent used to immobilize the test microorganism or enzyme is in an amount of between about $1 \times 10^{-6}$ and $1 \times 10^{-12}$ grams per microorganism or unit of enzyme.

22. The biological indicator of claim 21 wherein the amount of immobilizing agent used to immobilize the test microorganism or enzyme is between about $1 \times 10^{-6}$ and $1 \times 10^{-12}$ grams per microorganism or unit of enzyme.

23. The biological indicator of claim 1 wherein said indicator further comprises:

(c) contained within said outer container, an effective amount of an enzyme substrate capable of reacting in aqueous solution with said enzyme to produce a detectable enzyme-modified product.

24. The indicator of claim 23 wherein said enzyme substrate is in aqueous solution contained within a sealed, openable, gas and liquid impermeable inner container.

25. The indicator of claim 23 wherein said enzyme substrate is capable of reacting with said enzyme in an aqueous reaction medium to produce an enzyme-modified product which differs in luminescence, fluorescence, color or radioactivity from said enzyme substrate.

26. A test pack for determining the efficacy of a sterilization cycle in a sterilization chamber comprising the biological indicator of claim 1 within a test pack material or device.

27. The test pack of claim 26 wherein the test pack material is a 14 to 16 towel test pack meeting Association for the Advancement of Medical Instrumentation recommendations.

28. The test pack of claim 26 wherein the test pack device is a plastic syringe placed within a stack of towels and meeting Association for the Advancement of Medical Instrumentation recommendations.

29. The test pack of claim 26 wherein the test microorganism or enzyme has been immobilized to an extent capable of allowing a detectable amount of said immobilized microorganism or enzyme to survive or remain active following exposure, outside the test pack material or device, to at least a 5 minute steam sterilization cycle of 121° C. gravity, yet not capable of allowing any of said immobilized microorganism or enzyme to survive or remain active following an exposure, outside the test pack material or device, to said steam sterilization cycle for a time period of up to 15 minutes.

30. The test pack of claim 26 wherein the test microorganism or enzyme has been immobilized to an extent capable of allowing a detectable amount of said immobilized microorganism or enzyme to survive or remain active following exposure, outside the test pack material or device, to at least a 20 second steam sterilization cycle of 132° C. prevacuum, yet not capable of allowing any of said immobilized microorganism or enzyme to survive or remain active following an exposure, outside the test pack material or device, to said steam sterilization cycle for a time period of up to 6 minutes.

31. The test pack of claim 26 wherein the test microorganism or enzyme has been immobilized to an extent capable of allowing a detectable amount of said immobilized microorganism or enzyme to survive or remain active following exposure, outside the test pack material or device, to at least a 5 second steam sterilization cycle of 121° C. or 134° C. prevacuum, yet not capable of allowing any of said immobilized microorganism or enzyme to survive or remain active following an exposure, outside the test pack material or device, to said steam sterilization cycle for a time period of up to 2 minutes.

32. The test pack of claim 26 wherein the test microorganism or enzyme has been immobilized to an extent capable of allowing a detectable amount of said immobilized microorganism or enzyme to survive or remain active following exposure, outside the test pack material or device, to at least a 15 minute ethylene oxide sterilization cycle, yet not capable of allowing any of said immobilized microorganism or enzyme to survive or remain active following an exposure, outside the test pack material or device, to said ethylene oxide sterilization cycle for a time period of up to 90 minutes.

33. A method of increasing the thermostability of viable test microorganisms useful to monitor sterilization or active test enzymes useful to monitor sterilization within a biological indicator comprising immobilizing the test microorganism or test enzyme within the indicator by means selected from the group consisting of
(1) chemical reaction;
(2) adsorption onto a water-insoluble support material selected from the group consisting of a dextran derivative, silica gel, hydroxylapetite, and calcium carbonate;
(3) reaction with a water-insoluble support material capable of forming covalent or ionic bonds to the test microorganism or test enzyme;
(4) entrapping the microorganism or enzyme within a crosslinked polymer gel matrix comprising non-ionic polymer-forming materials which are non-reactive with the microorganism or enzyme;
(5) crosslinking with a crosslinking agent capable of forming intra- or inter-molecular crosslinks between the test microorganisms or test enzyme; and
(6) microencapsulation;
such immobilization being to an extent capable of allowing a detectable amount of said immobilized microorganism or enzyme to survive or remain active following an exposure to the sterilization cycle which is sublethal to the test microorganism when contained in a test pack commonly used to monitor sterilization, and incapable of allowing any detectable amount of immobilized microorganism or enzyme to survive or remain active following an exposure to the sterilization cycle which is lethal to the test microorganisms when contained in the test pack commonly used to monitor sterilization.

34. The method of claim 33 wherein the biological indicator is adapted to monitor an ethylene oxide sterilization cycle and the test microorganism or enzyme is immobilized with a chemical immobilizing agent selected from the group consisting of alditols, monosaccharides, polysaccharides, polylactams, and polymeric alcohols selected from the group consisting of polyvinyl alcohol, glycols and diols.

35. The method of claim 34 wherein the immobilizing agent used to immobilize the test microorganisms or enzymes is in an amount of between about $1\times10^{-6}$ and $1\times10^{-12}$ grams per microorganism or unit of enzyme.

36. The method of claim 35 wherein the amount of immobilizing agent used to immobilize the test microorganisms or enzymes is between about $1\times10^{-6}$ and $1\times10^{-12}$ grams per microorganism or unit of enzyme.

37. The method of claim 33 wherein the biological indicator is adapted to monitor a steam sterilization cycle and the test microorganism or enzyme is immobilized with a chemical immobilizing agent selected from the group consisting of alditols, disaccharides, trisaccharides, and polymeric alcohols selected from the group consisting of polyvinyl alcohol, glycols and diols.

38. The method of claim 37 wherein the test microorganisms or enzymes are immobilized by adsorption onto a water-insoluble support material.

39. The method of claim 38 wherein the water-insoluble support material is capable of absorbing at least $1\times10^2$ test microorganisms or 0.1 unit of test enzyme.

40. The method of claim 37 wherein the test microorganisms or enzymes are immobilized by a water-insoluble support material capable of forming covalent or ionic bonds to the test microorganisms or test enzymes.

41. The method of claim 40 wherein the water-insoluble support material is capable of forming covalent or ionic bonds to at least $1\times10^2$ test microorganisms or 0.1 unit of test enzyme.

42. The method Of claim 33 wherein the test microorganisms or test enzymes are immobilized by entrapping the microorganism or enzyme within a crosslinked polymer gel matrix comprising non-ionic polymer-forming materials which are non-reactive with the microorganism or enzyme.

43. The method of claim 42 wherein at least $1\times10^2$ test microorganisms or 0.1 unit of test enzyme is entrapped within the crosslinked polymer gel matrix.

44. The method of claim 33 wherein the test microorganisms or enzymes are immobilized by a crosslinking agent capable of forming intra- or inter-molecular cross links between the test microorganisms or test enzyme.

45. The method of claim 44 wherein the crosslinking agent is capable of forming intra- or inter-molecular cross links between at least $1\times10^2$ test microorganisms or 0.1 unit of test enzyme.

46. The method of claim 33 wherein the test microorganisms or test enzymes are immobilized by microencapsulation.

47. The method of claim 46 wherein at least $1\times10^2$ test microorganisms or 0.1 unit of test enzyme is immobilized.

48. An improved biological indicator comprising
(a) an outer container having liquid impermeable and substantially non-gas adsorptive walls, said container having at least one opening therein;
(b) contained within said outer container a detectable amount of
(1) a viable test microorganism useful to monitor ethylene oxide sterilization or
(2) another source of an active test enzyme useful to monitor ethylene oxide sterilization,
wherein the improvement comprises immobilizing the test microorganism or enzyme by means selected from the group consisting of
(1) chemical reaction;
(2) adsorption onto a water-insoluble support material selected from the group consisting of a dextran derivative, silica gel, hydroxylapetite, and calcium carbonate;
(3) reaction with a water-insoluble support material capable of forming covalent or ionic bonds to the test microorganism or test enzyme;
(4) entrapping the microorganism or enzyme within a crosslinked polymer gel matrix comprising non-ionic polymer-forming materials which are non-reactive with the microorganism or enzyme;

(5) crosslinking with a crosslinking agent capable of forming intra- or inter-molecular crosslinks between the test microorganisms or test enzyme; and (6) microencapsulation;

such immobilization being to an extent capable of allowing a detectable amount of said immobilized microorganism or enzyme to survive or remain active following at least a 15 minute exposure to the ethylene oxide sterilization cycle, yet not capable of allowing any of the immobilized microorganism or enzyme to survive or remain active following an exposure to the ethylene oxide sterilization cycle for a time period of up to 250 minutes.

49. The biological indicator of claim 48 wherein the immobilization of the microorganism or enzyme is sufficient to allow a detectable amount of immobilized microorganism or enzyme to survive or remain active following at least a 20 minute exposure to an ethylene oxide sterilization cycle of 600 milligrams per liter of ethylene oxide, at 54° C. and 60% relative humidity, yet not capable of allowing any immobilized microorganism or enzyme to survive or remain active following an exposure to the ethylene oxide sterilization cycle for a period of up to 60 minutes.

50. The biological indicator of claim 48 wherein the immobilization of the test microorganism or enzyme is sufficient to allow a detectable amount of immobilized microorganism or enzyme to survive or remain active following at least a 15 minute exposure to an ethylene oxide sterilization cycle of 800 milligrams per liter of ethylene oxide, at 37° C. and 60% relative humidity, yet not capable of allowing any immobilized microorganism or enzyme to survive or remain active following an exposure to the ethylene oxide sterilization cycle for a period of up to 120 minutes.

51. An improved method for determining the effectiveness of a sterilization cycle, comprising the steps of:

(a) subjecting to said sterilization cycle a detectable amount of test microorganisms useful to monitor the sterilization cycle or test enzymes useful to monitor the sterilization cycle, (b) following the completion of the sterilization cycle, incubating (1) any viable test microorganisms with an aqueous nutrient medium capable of promoting growth of said viable microorganisms and a detector material capable of undergoing a detectable change in response to growth of the microorganisms; or (2) any active test enzymes with an effective amount of an enzyme substrate capable of reacting with active enzymes to produce a detectable enzyme-modified product;

said incubation being for a time period and under conditions sufficient to promote growth of the microorganisms or reaction of active enzymes with the enzyme substrate; wherein the improvement comprises immobilizing the test microorganisms or enzymes prior to being subjected to the sterilization cycle by means selected from the group consisting of (1) chemical reaction;

(2) adsorption onto a water-insoluble support material selected from the group consisting of a dextran derivative, silica gel, hydroxylapetite, and calcium carbonate;

(3) reaction with a water-insoluble support material capable of forming covalent or ionic bonds to the test microorganism or test enzyme;

(4) entrapping the microorganism or enzyme within a crosslinked polymer gel matrix comprising non-ionic polymer-forming materials which are non-reactive with the microorganism or enzyme;

(5) crosslinking with a crosslinking agent capable of forming intra- or inter-molecular crosslinks between the test microorganisms or test enzyme; and (6) microencapsulation;

such immobilization being to an extent capable of allowing a detectable amount of said immobilized microorganism or enzyme to survive or remain active following an exposure to the sterilization cycle which is sublethal to the test microorganism when contained in a test pack commonly used to monitor sterilization, and incapable of allowing any detectable amount of immobilized microorganism or enzyme to survive or remain active following an exposure to the sterilization cycle which is lethal to the test microorganism when contained in the test pack commonly used to monitor sterilization.

52. The method of claim 51 wherein at least $1 \times 10^2$ test microorganisms or 0.1 unit of test enzymes are immobilized.

53. The method of claim 51 wherein said sterilization cycle is provided by saturated steam, dry heat, gas, liquid or radiation.

54. An improved biological indicator comprising (a) an outer container having liquid impermeable walls, said container having at least one opening therein;

(b) contained within said outer container a detectable amount of (1) a viable test microorganism useful to monitor steam sterilization or (2) another source of an active test enzyme useful to monitor steam sterilization, wherein the improvement comprises immobilizing the test microorganism or enzyme by means selected from the group consisting of (1) chemical reaction;

(2) adsorption onto a water-insoluble support material selected from the group consisting of a dextran derivative, silica gel, hydroxylapetite, and calcium carbonate;

(3) reaction with a water-insoluble support material capable of forming covalent or ionic bonds to the test microorganism or test enzyme;

(4) entrapping the microorganism or enzyme within a crosslinked polymer gel matrix comprising non-ionic polymer-forming materials which are non-reactive with the microorganism or enzyme;

(5) crosslinking with a crosslinking agent capable of forming intra- or inter-molecular crosslinks between the test microorganisms or test enzyme; and (6) microencapsulation;

such immobilization being to an extent capable of allowing a detectable amount of said immobilized microorganism or enzyme to survive or remain active following at least a 15 minutes exposure to a steam sterilization cycle of 121° C. gravity, yet not capable of allowing any of said immobilized microorganism or enzyme to survive or remain active following an exposure to said steam sterilization cycle for a time period of up to 45 minutes.

55. An improved biological indicator comprising (a) an outer container having liquid impermeable walls, said container having at least one opening therein;

(b) contained within said outer container a detectable amount of (1) a viable test microorganism useful to monitor steam sterilization or (2) another source of an active test enzyme useful to monitor steam sterilization, wherein the improvement comprises immobilizing the test microorganism or enzyme by means selected from the group consisting of
(1) chemical reaction;
(2) adsorption onto a water-insoluble support material selected from the group consisting of a dextran derivative, silica gel, hydroxylapetite, and calcium carbonate;
(3) reaction with a water-insoluble support material capable of forming covalent or ionic bonds to the test microorganism or test enzyme;
(4) entrapping the microorganism or enzyme within a crosslinked polymer gel matrix comprising non-ionic polymer-forming materials which are non-reactive with the microorganism or enzyme;
(5) crosslinking with a crosslinking agent capable of forming intra- or inter-molecular crosslinks between the test microorganisms or test enzyme; and
(6) microencapsulation;

such immobilization being to an extent capable of allowing a detectable amount of said immobilized microorganism or enzyme to survive or remain active following at least a 5 minute exposure to a stem sterilization cycle of 121° C. prevacuum, yet not capable of allowing any of said immobilized microorganism or enzyme to survive or remain active following an exposure to said steam sterilization cycle for a time period of up to 15 minutes.

56. An improved biological indicator comprising
(a) an outer container having liquid impermeable walls, said container having at least one opening therein;
(b) contained within said outer container a detectable amount of
(1) a viable test microorganism useful to monitor steam sterilization or
(2) another source of an active test enzyme useful to monitor steam sterilization, wherein the improvement comprises immobilizing the test microorganism or enzyme by means selected from the group consisting of
(1) chemical reaction;
(2) adsorption onto a water-insoluble support material selected from the group consisting of a dextran derivative, silica gel, hydroxylapetite, and calcium carbonate;
(3) reaction with a water-insoluble support material capable of forming covalent or ionic bonds to the test microorganism or test enzyme;
(4) entrapping the microorganism or enzyme within a crosslinked polymer gel matrix comprising non-ionic polymer-forming materials which are non-reactive with the microorganism or enzyme;
(5) crosslinking with a crosslinking agent capable of forming intra- or inter-molecular crosslinks between the test microorganisms or test enzyme; and
(6) microencapsulation;

such immobilization being to an extent capable of allowing a detectable amount of said immobilized microorganism or enzyme to survive or remain active following at least a 15 second exposure to a steam sterilization cycle of 132° C. prevacuum, yet not capable of allowing any of said immobilized microorganism or enzyme to survive or remain active following an exposure to said steam sterilization cycle of up to 15 minutes.

57. An improved biological indicator comprising
(a) an outer container having liquid impermeable walls, said container having at least one opening therein;
(b) contained within said outer container a detectable amount of
(1) a viable test microorganism useful to monitor steam sterilization or
(2) another source of an active test enzyme useful to monitor steam sterilization, wherein the improvement comprises immobilizing the test microorganism or enzyme by means selected from the group consisting of
(1) chemical reaction;
(2) adsorption onto a water-insoluble support material selected from the group consisting of a dextran derivative, silica gel, hydroxylapetite, and calcium carbonate;
(3) reaction with a water-insoluble support material capable of forming covalent or ionic bonds to the test microorganism or test enzyme;
(4) entrapping the microorganism or enzyme within a crosslinked polymer gel matrix comprising non-ionic polymer-forming materials which are non-reactive with the microorganism or enzyme;
(5) crosslinking with a crosslinking agent capable of forming intra- or inter-molecular crosslinks between the test microorganisms or test enzyme; and
(6) microencapsulation;

such immobilization being to an extent capable of allowing a detectable amount of said immobilized microorganism or enzyme to survive or remain active following at least a 2 second exposure to a steam sterilization cycle of 134° C. prevacuum, yet not capable of allowing any of said immobilized microorganism or enzyme to survive or remain active following an exposure to said steam sterilization cycle for a time period of up to 10 minutes.

58. An improved unitary biological indicator comprising
(a) an outer container having liquid impermeable and substantially gas non-adsorptive walls, said container having at least one opening therein;
(b) a gas-transmissive, semi-porous means covering said opening;
(c) contained within said outer container a detectable amount of microorganisms selected from the group consisting of *Bacillus stearothermophilus* and *Bacillus subtilis;*
(d) a sealed, openable gas and liquid impermeable inner container containing a composition consisting of
(1) aqueous nutrient medium capable, with incubation, of promoting growth of viable test microorganisms;
(2) an enzyme substrate capable of reacting in the presence of an aqueous medium with said enzyme to produce a detectable enzyme-modified product; and
(3) a detector material capable of undergoing a visible color change in response to growth of said test microorganism, said inner container being disposed in said outer container and said inner container, when opened, permitting said composition to contact said immobilized microorganism; wherein the improvement comprises immobilizing the microorganisms by means selected from the group consisting of
(1) chemical reaction;
(2) adsorption onto a water-insoluble support material selected from the group consisting of a dextran derivative, silica gel, hydroxylapetite, and calcium carbonate;

(3) reaction with a water-insoluble support material capable of forming covalent or ionic bonds to the test microorganism or test enzyme;

(4) entrapping the microorganism or enzyme within a crosslinked polymer gel matrix comprising non-ionic polymer-forming materials which are non-reactive with the microorganism or enzyme;

(5) crosslinking with a crosslinking agent capable of forming intra- or inter-molecular crosslinks between the test microorganisms or test enzyme; and (6) microencapsulation;

such immobilization being to an extent capable of allowing a detectable amount of said immobilized microorganism or enzyme to survive or remain active following an exposure to the sterilization cycle which is sublethal to the test microorganism when contained in a test pack commonly used to monitor sterilization, and incapable of allowing any detectable amount of immobilized microorganism or enzyme to survive or remain active following an exposure to the sterilization cycle which is lethal to the test microorganism when contained in the test pack commonly used to monitor sterilization.

59. A method of increasing the thermostability of viable test microorganisms useful to monitor sterilization or active test enzymes useful to monitor sterilization within a biological indicator comprising immobilizing at least $1 \times 10^2$ of the test microorganisms or at least 0.1 unit of the test enzyme within the indicator by means selected from the group consisting of (1) chemical reaction;

(2) adsorption onto a water-insoluble support material selected from the group consisting of a dextran derivative, silica gel, hydroxylapetite, and calcium carbonate;

(3) reaction with a water-insoluble support material capable of forming covalent or ionic bonds to the test microorganism or test enzyme;

(4) entrapping the microorganism or enzyme within a crosslinked polymer gel matrix comprising non-ionic polymer-forming materials which are non-reactive with the microorganism or enzyme;

(5) crosslinking with a crosslinking agent capable of forming intra- or inter-molecular crosslinks between the test microorganisms or test enzyme; and (6) microencapsulation.

60. An improved test pack wherein said test pack comprises:

(a) an openable paper box enclosure dimensioned to be placed within a sterilizer;

(b) an open container made of paper with a thermoplastic coating on its exterior surfaces, said open paper container placed within said box and having dimensions only slightly smaller than said box;

(c) a stack of semi-porous sheets filling said open container, said stack of semi-porous sheets having a cavity formed therein;

(d) a biological indicator placed within the cavity in said stack of semi-porous sheets, the biological indicator comprising:

(1) an outer container having liquid impermeable walls, said container having at least one opening therein;

(2) contained within said outer container a detectable amount of (i) a viable test microorganism useful to monitor a sterilization cycle or (ii) another source of an active test enzyme useful to monitor the sterilization cycle; and (3) contained within said outer container, an effective amount of an enzyme substrate capable of reacting in aqueous solution with active enzyme to produce a detectable enzyme-modified product;

wherein the improvement comprises immobilizing the test microorganism or enzyme by means selected from the group consisting of (1) chemical reaction;

(2) adsorption onto a water-insoluble support material selected from the group consisting of a dextran derivative, silica gel, hydroxylapetite, and calcium carbonate;

(3) reaction with a water-insoluble support material capable of forming covalent or ionic bonds to the test microorganism or test enzyme;

(4) entrapping the microorganism or enzyme within a crosslinked polymer gel matrix comprising non-ionic polymer-forming materials which are non-reactive with the microorganism or enzyme;

(5) crosslinking with a crosslinking agent capable of forming intra- or inter-molecular crosslinks between the test microorganisms or test enzyme; and (6) microencapsulation;

such immobilization being to an extent capable of allowing a detectable amount of said immobilized microorganism or enzyme to survive or remain active following an exposure to the sterilization cycle which is sublethal to the test microorganism when contained in a test pack commonly used to monitor sterilization, and incapable of allowing any detectable amount of immobilized microorganism or enzyme o survive or remain active following an exposure to the sterilization cycle which is lethal to the test microorganism hen contained in the test pack commonly used to monitor sterilization.

* * * * *

UNITED STATES PATENT AND TRADEMARK OFFICE
CERTIFICATE OF CORRECTION

PATENT NO.: 5,739,004
DATED: April 14, 1998
INVENTOR(S): Lewis P. Woodson

It is certified that error appears in the above-identified patent and that said Letters Patent is hereby corrected as shown below:

In Col. 54, Line 22, delete "Of" and insert --of--.

In Col. 56, Line 55, delete "minutes" and insert --minute--.

In Col. 57, Line 25, delete "stem" and insert -- steam --.

Signed and Sealed this

Ninth Day of March, 1999

Attest:

Q. TODD DICKINSON

Attesting Officer

Acting Commissioner of Patents and Trademarks